United States Patent
Schultz

(10) Patent No.: US 11,363,841 B2
(45) Date of Patent: Jun. 21, 2022

(54) POSTURE CONTROL AND THERAPY SYSTEM

(71) Applicant: AlignMed, Inc., Santa Ana, CA (US)

(72) Inventor: William J. Schultz, Newport Beach, CA (US)

(73) Assignee: Alignmed, Inc., Santa Ana, CA (US)

( * ) Notice: Subject to any disclaimer, the term of this patent is extended or adjusted under 35 U.S.C. 154(b) by 329 days.

(21) Appl. No.: 15/855,650

(22) Filed: Dec. 27, 2017

(65) Prior Publication Data

US 2018/0132543 A1    May 17, 2018

Related U.S. Application Data

(63) Continuation of application No. 14/455,093, filed on Aug. 8, 2014, now Pat. No. 9,883,703.

(60) Provisional application No. 61/863,858, filed on Aug. 8, 2013.

(51) Int. Cl.
  *A41D 1/00* (2018.01)
  *A61F 5/02* (2006.01)

(52) U.S. Cl.
  CPC ............... *A41D 1/00* (2013.01); *A61F 5/026* (2013.01)

(58) Field of Classification Search
  CPC ................................. A41D 1/00; A61F 5/026
  USPC ............................................................ 2/88
  See application file for complete search history.

(56) References Cited

U.S. PATENT DOCUMENTS

| | | | | |
|---|---|---|---|---|
| 2,481,396 A | * | 9/1949 | Cohen ...................... | A41C 1/08 450/95 |
| 5,109,546 A | * | 5/1992 | Dicker ..................... | A41D 1/08 2/70 |
| 5,157,790 A | * | 10/1992 | Aldridge ............ | A41D 13/0525 2/227 |
| 5,188,585 A | * | 2/1993 | Peters ..................... | A61F 5/028 128/100.1 |
| 5,201,074 A | * | 4/1993 | Dicker ............... | A41D 13/0015 2/227 |
| 5,205,815 A | * | 4/1993 | Saunders ........... | A41D 13/0525 450/150 |
| 5,399,150 A | * | 3/1995 | Saunders ........... | A41D 13/0525 128/100.1 |

(Continued)

*Primary Examiner* — Alissa L Hoey
*Assistant Examiner* — Patrick J. Lynch
(74) *Attorney, Agent, or Firm* — Fox Rothschild LLP; Kari L. Barnes

(57) ABSTRACT

A garment for wear by a person and a garment system of garments includes bands and elastic portions to apply tension and support to muscle groups when the garment is worn by a wearer. The garments include a vest with crossed back bands within the garment that are selectively fastenable to the exterior of the vest to exert tension from the shoulders to the hips. Also included is a cape with shoulder straps and hip straps to apply further tension when attached to the vest or another garment. A shirt includes a central back panel and one or more shoulder straps, the central panel extending to side straps at the hip. Shorts with a spiral strap apply tension from the body core to the leg of the wearer. Shirts and tops for women including for maternity wear include support specific to a woman's body. Some of the shirts, tops, shorts and vests have wearer adjustable straps to vary the tension applied by the straps. Auxiliary straps with fasteners are available for applying additional tension when mounted on the garments.

19 Claims, 23 Drawing Sheets

(56) References Cited

U.S. PATENT DOCUMENTS

| | | | | |
|---|---|---|---|---|
| 5,445,601 A * | 8/1995 | Harlow | A61F 5/028 | 128/845 |
| 5,465,428 A * | 11/1995 | Earl | A63B 21/0552 | 2/227 |
| 5,471,680 A * | 12/1995 | Vesterinen | A41D 13/0525 | 2/338 |
| 5,611,084 A * | 3/1997 | Garry | A41D 13/0525 | 2/102 |
| 5,819,322 A * | 10/1998 | Dicker | A41D 13/0015 | 2/456 |
| 6,108,819 A * | 8/2000 | DeBaene | A41D 1/067 | 2/227 |
| 6,129,638 A * | 10/2000 | Davis | A63B 69/0059 | 473/215 |
| 6,430,752 B1 * | 8/2002 | Bay | A41C 1/003 | 2/228 |
| 6,585,673 B1 * | 7/2003 | Bass | A61F 7/02 | 128/845 |
| D507,858 S * | 8/2005 | Ota | D2/731 | |
| D508,304 S * | 8/2005 | Ota | D2/731 | |
| 7,037,284 B2 * | 5/2006 | Lee | A61F 5/028 | 602/19 |
| 7,765,619 B2 * | 8/2010 | Jaccard | A61F 5/028 | 128/99.1 |
| 7,882,574 B2 * | 2/2011 | Arsenault | A61F 5/028 | 2/227 |
| 8,707,463 B2 * | 4/2014 | Orloff | A41D 13/0015 | 2/22 |
| 8,910,317 B2 * | 12/2014 | Decker | A41D 13/0015 | 2/227 |
| 9,314,363 B2 * | 4/2016 | Ingimundarson | A61F 5/0193 | |
| 9,393,144 B2 * | 7/2016 | Ingimundarson | A61F 5/0193 | |
| 9,895,569 B2 * | 2/2018 | Yao | A63B 69/0028 | |
| 10,022,258 B2 * | 7/2018 | Arsenault | A61F 5/028 | |
| 10,039,330 B2 * | 8/2018 | Tanaka | A41D 1/08 | |
| D875,351 S * | 2/2020 | Harris | D2/731 | |
| 2003/0028952 A1 * | 2/2003 | Fujii | A41D 13/0015 | 2/400 |
| 2004/0132380 A1 * | 7/2004 | Kihara | A61F 5/028 | 450/154 |
| 2005/0229295 A1 * | 10/2005 | Chun | A41D 13/0506 | 2/467 |
| 2005/0268379 A1 * | 12/2005 | MacGeorge | A41F 9/02 | 2/400 |
| 2007/0094775 A1 * | 5/2007 | Chun | A41C 1/08 | 2/255 |
| 2011/0000005 A1 * | 1/2011 | Brown | A61F 5/0111 | 2/227 |
| 2014/0200121 A1 * | 7/2014 | von Hoffmann | A63B 23/0482 | 482/124 |
| 2019/0239579 A1 * | 8/2019 | Stricker | A63B 21/0428 | |
| 2020/0085123 A1 * | 3/2020 | Achtymichuk | A63B 21/0407 | |

* cited by examiner

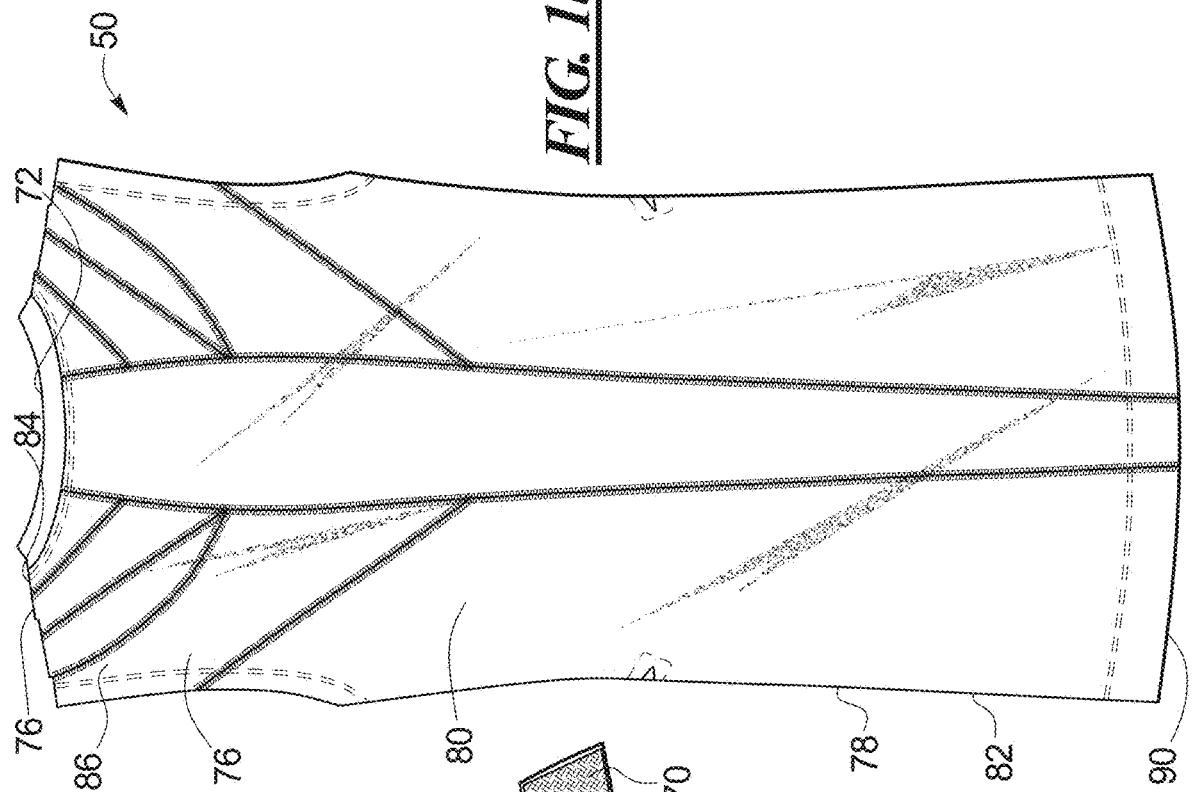
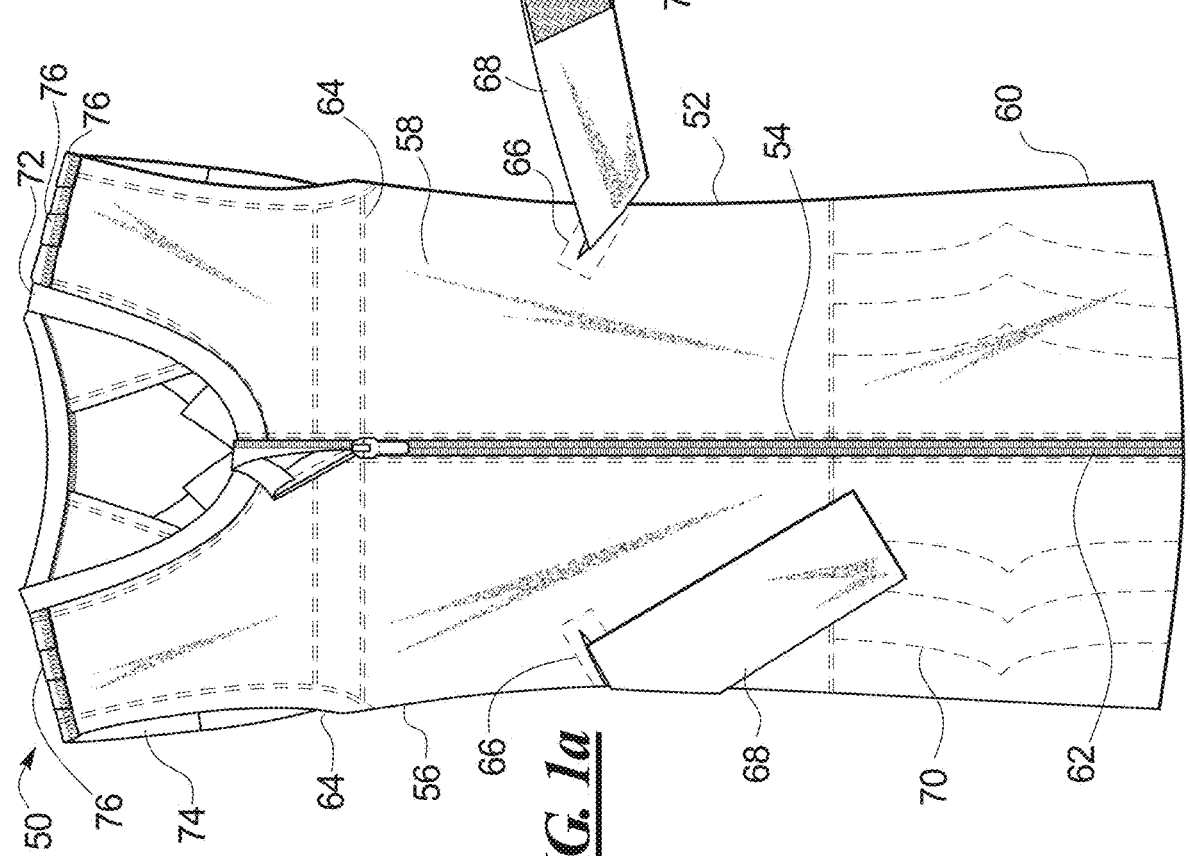

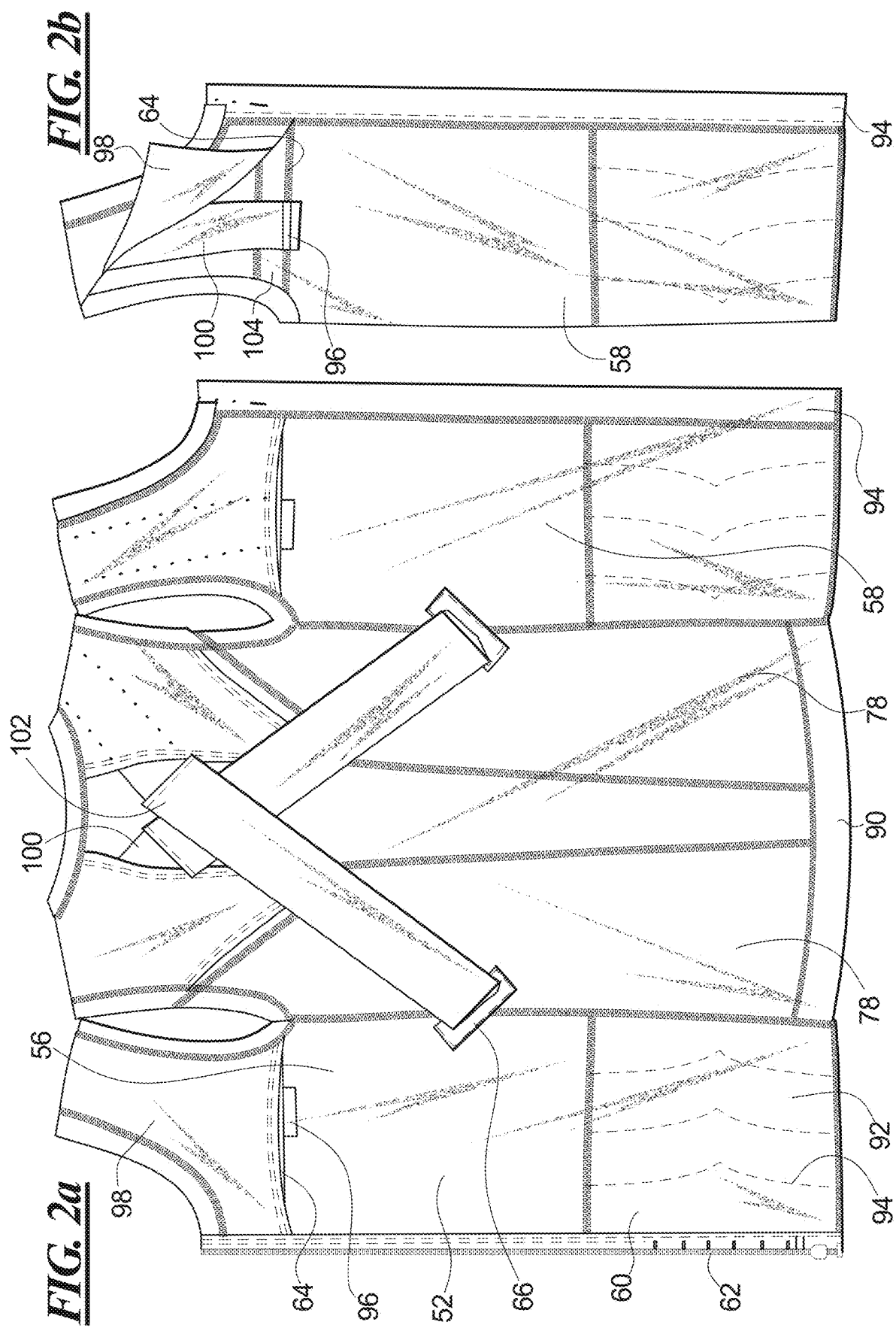

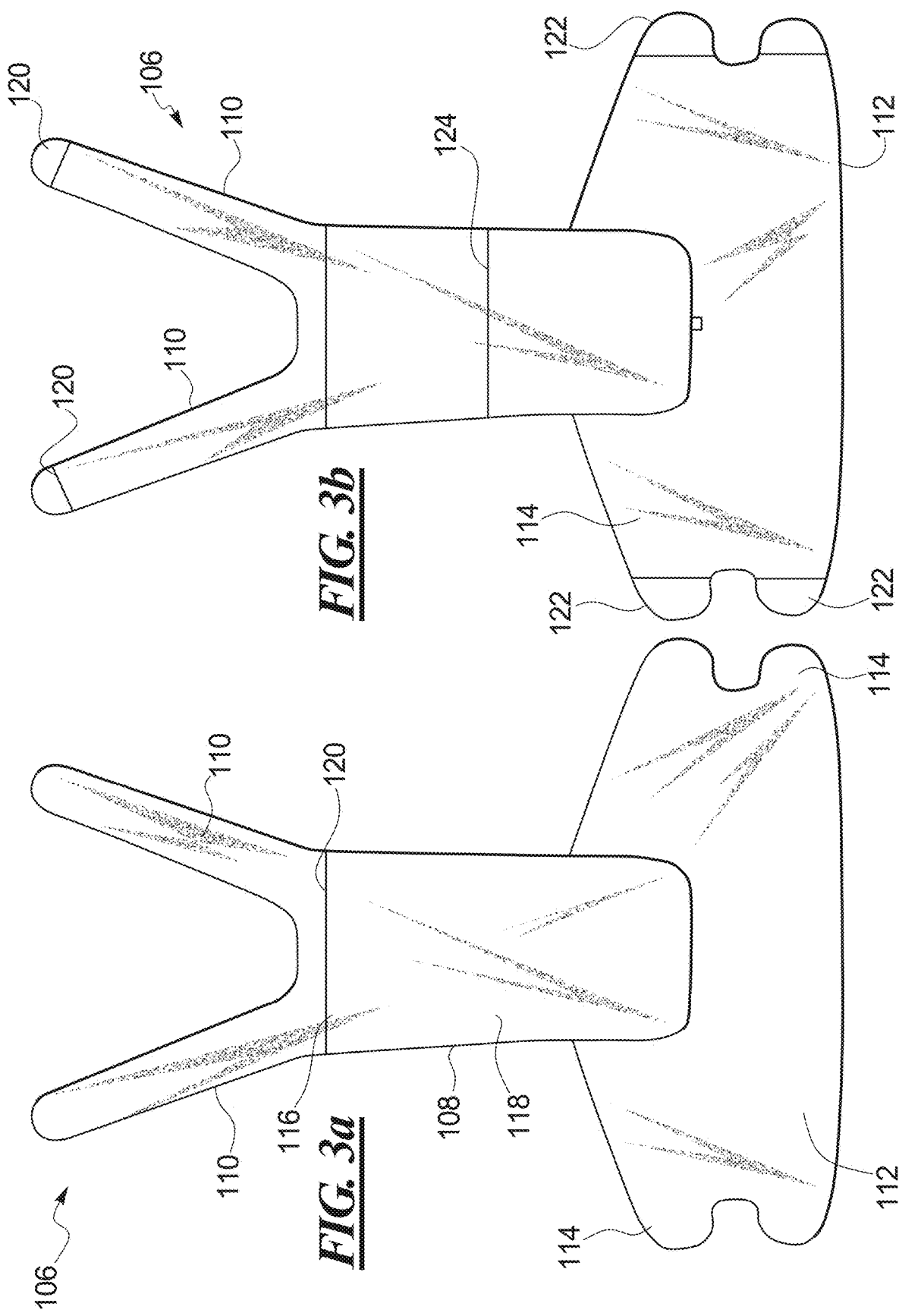

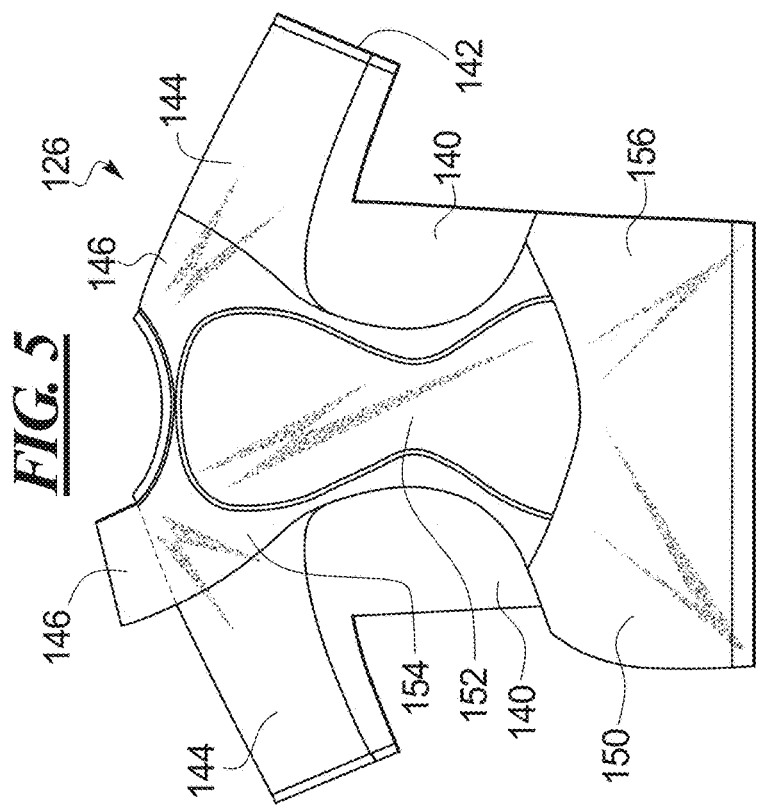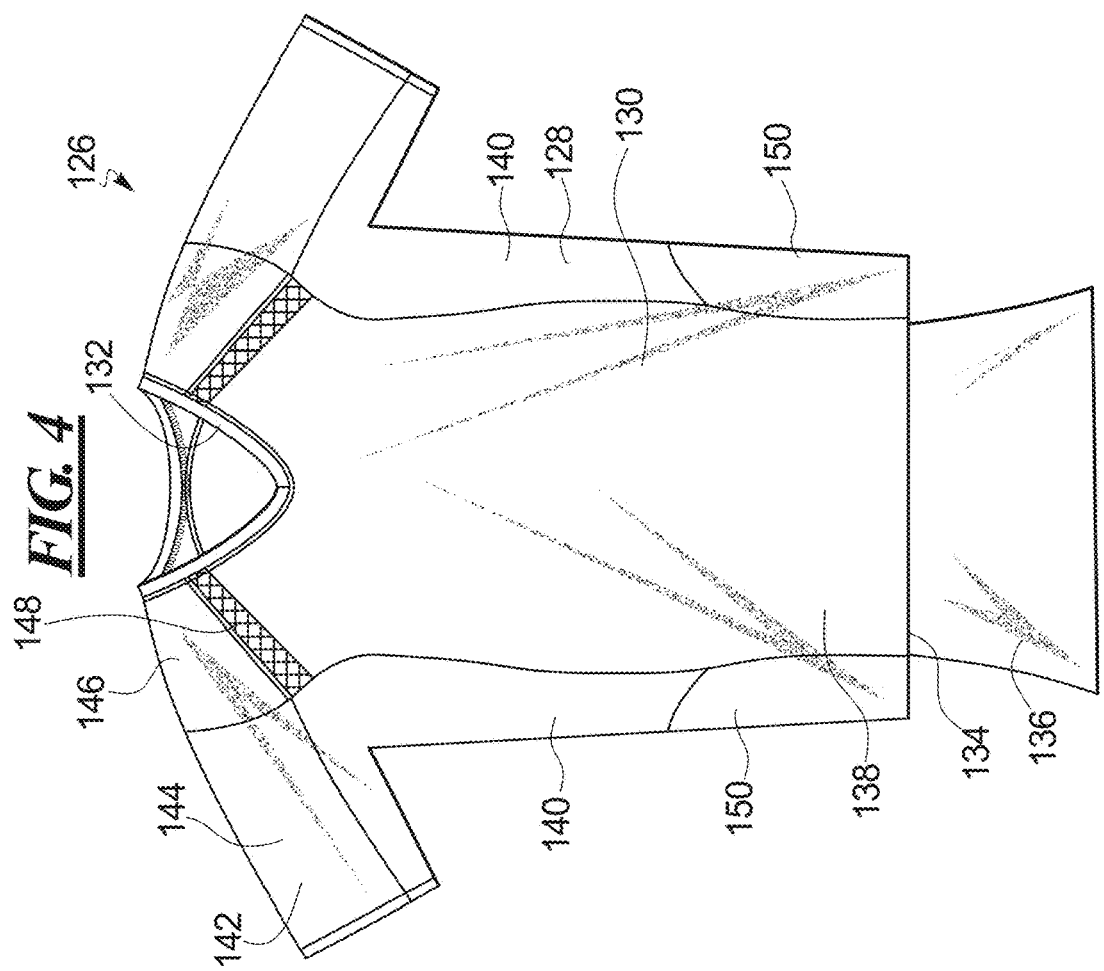

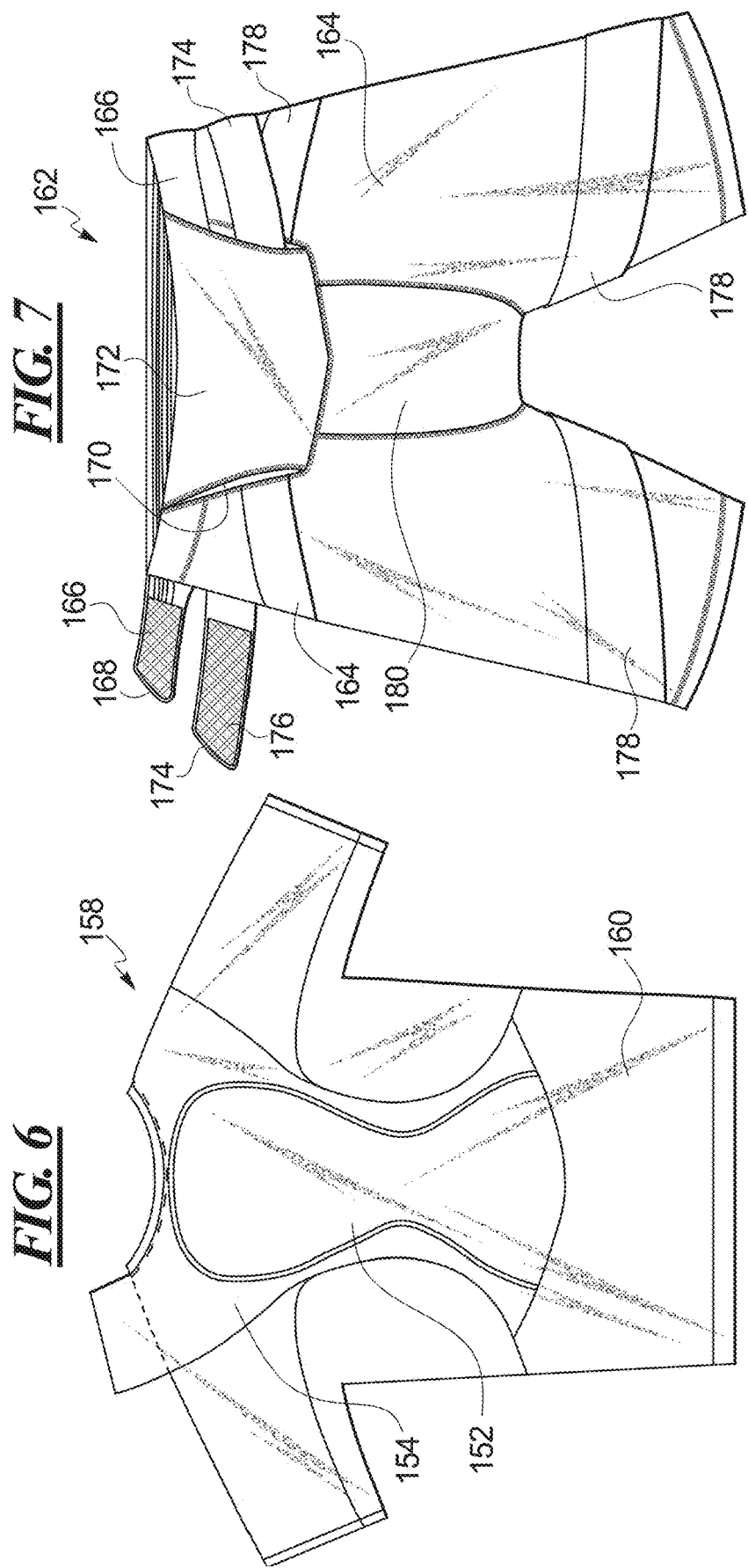

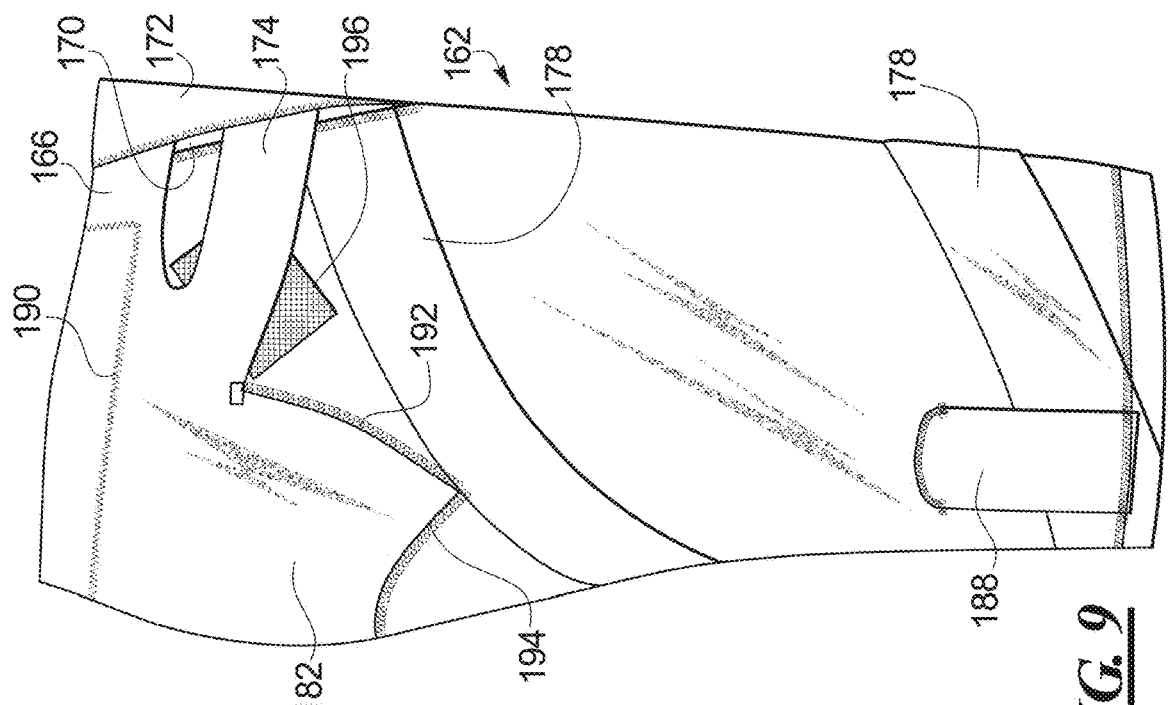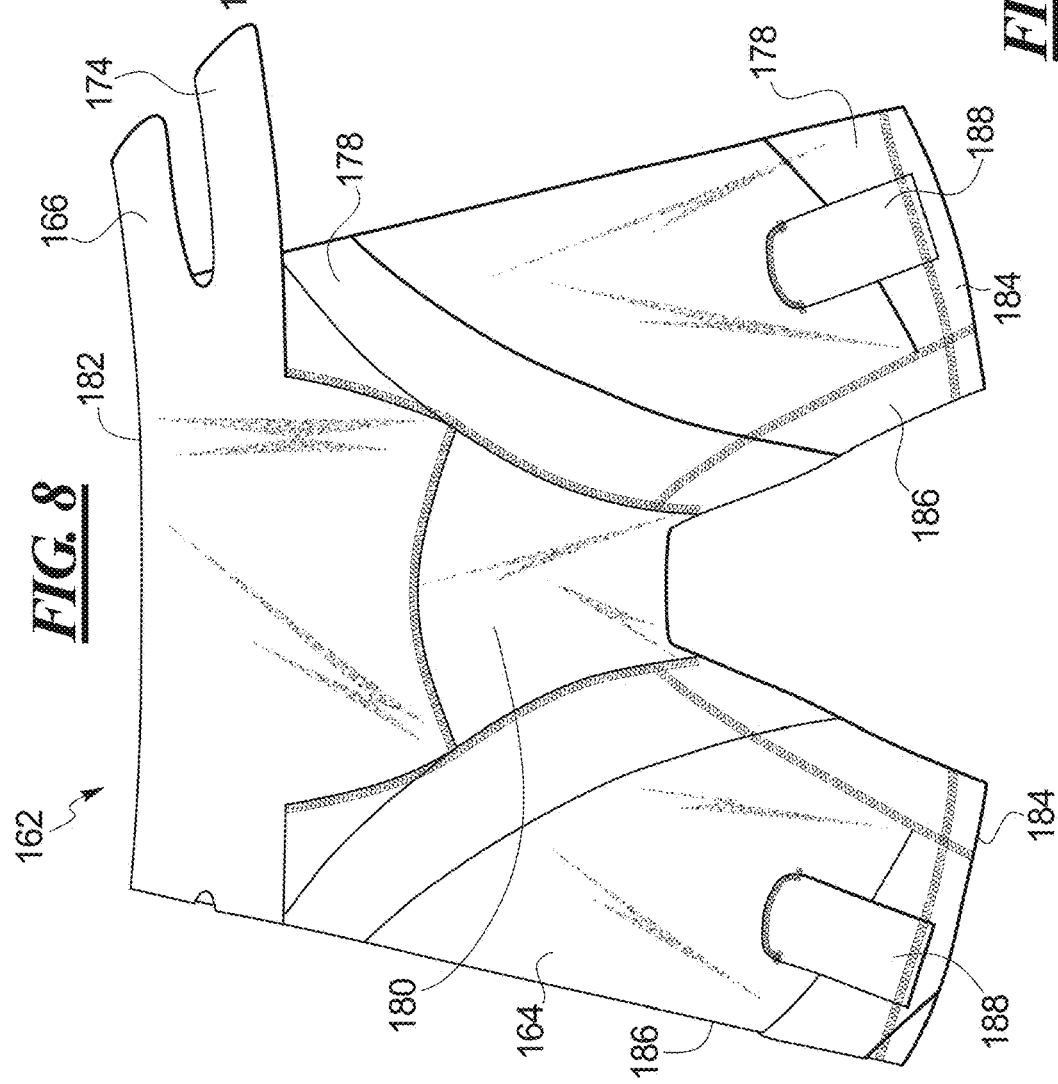

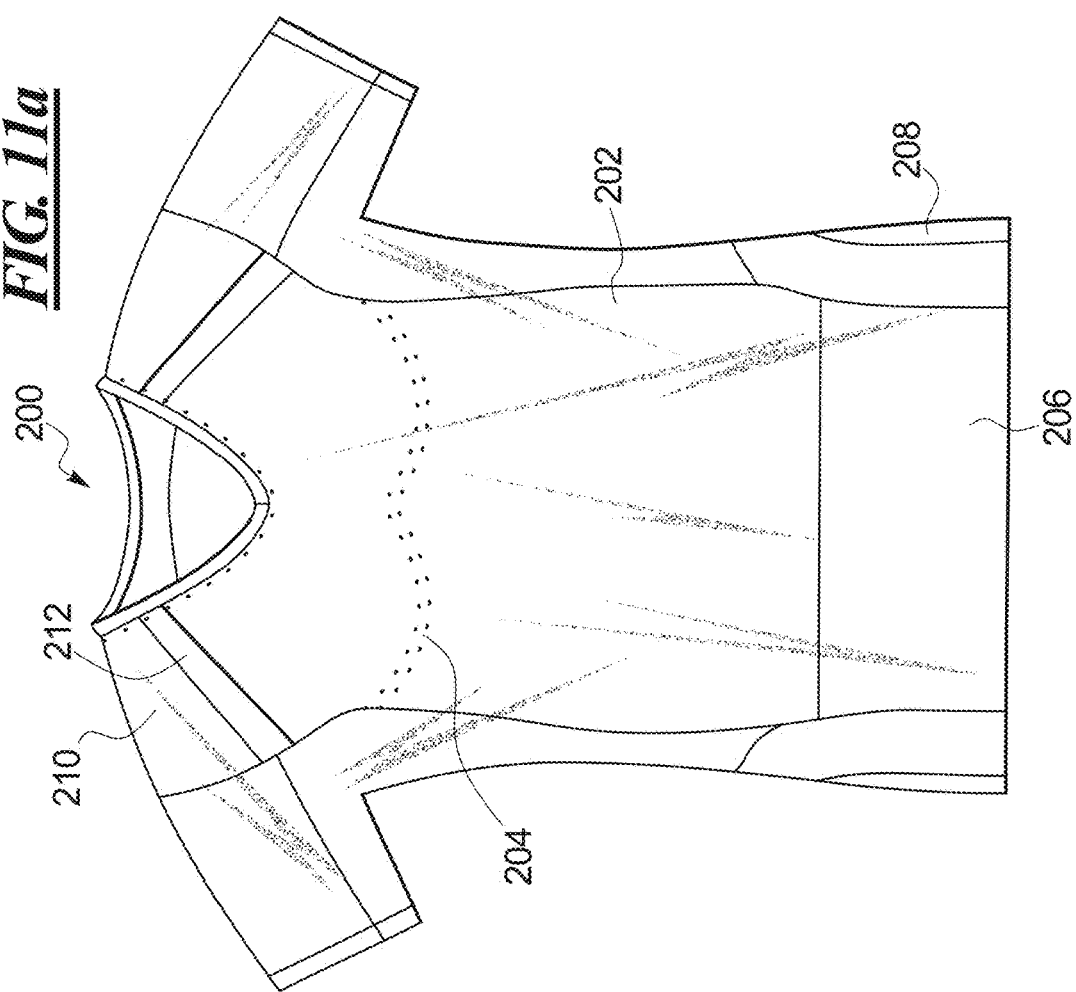
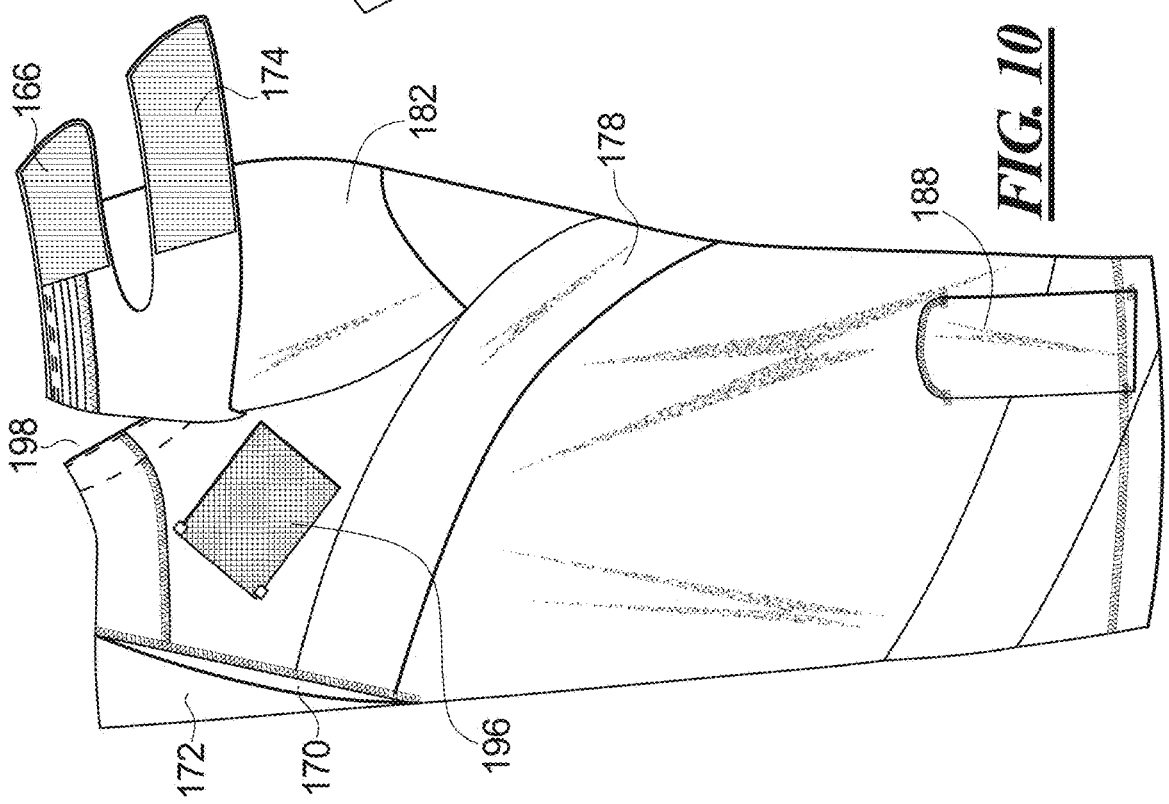

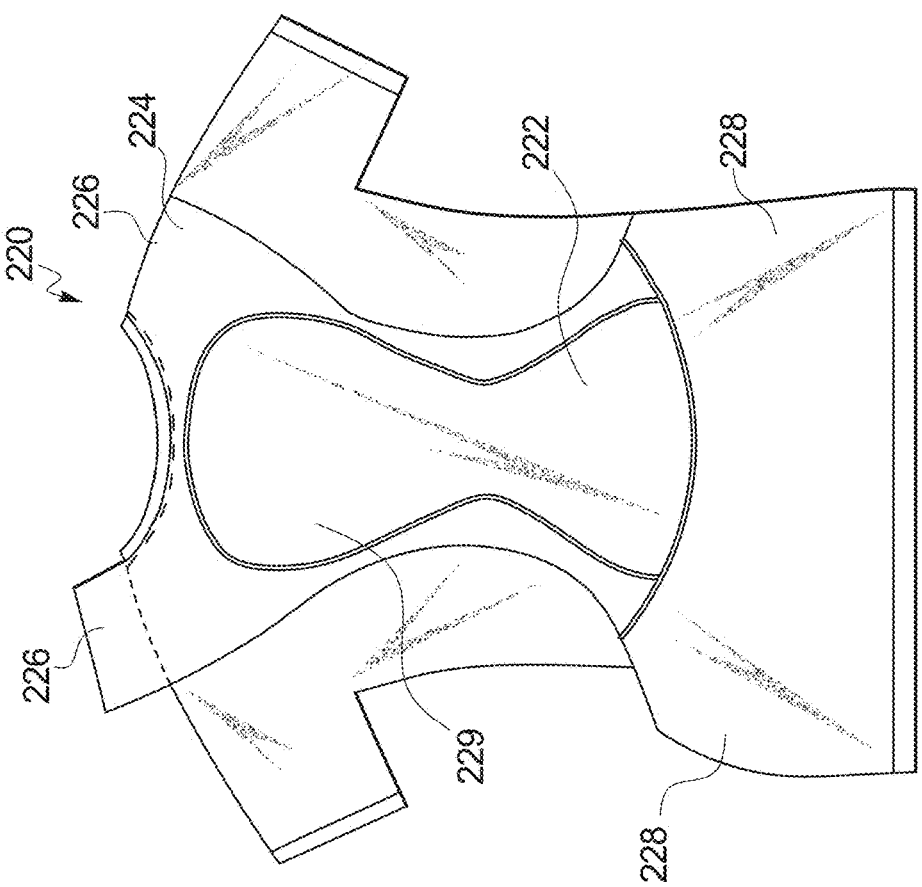
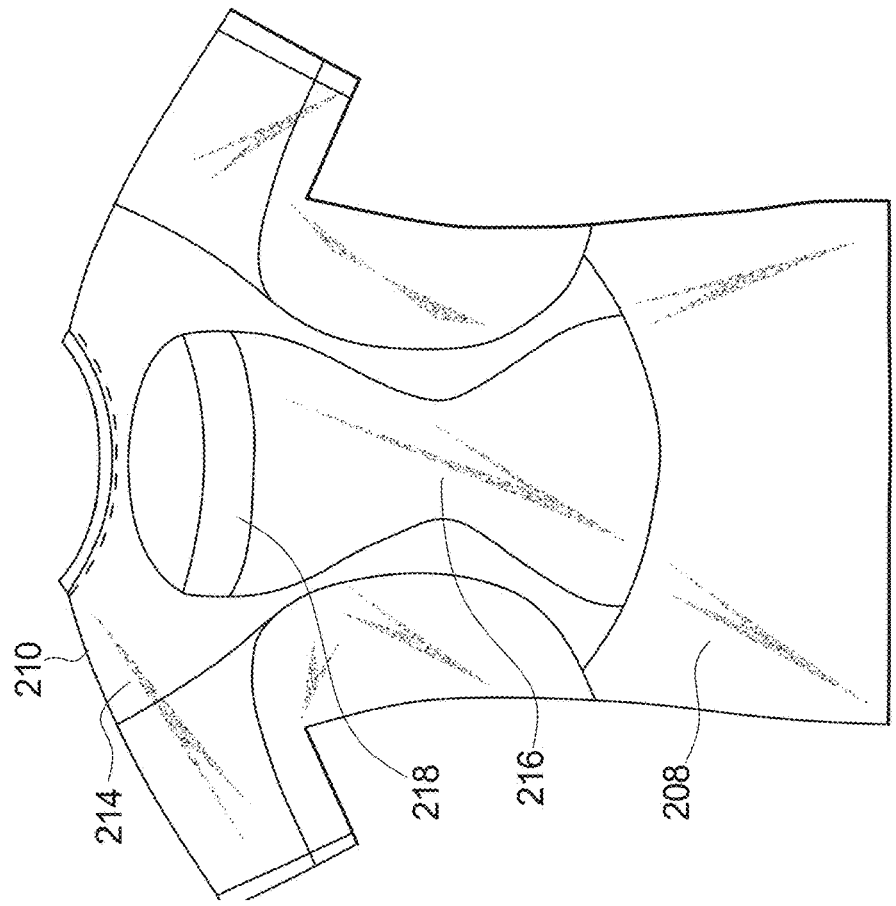

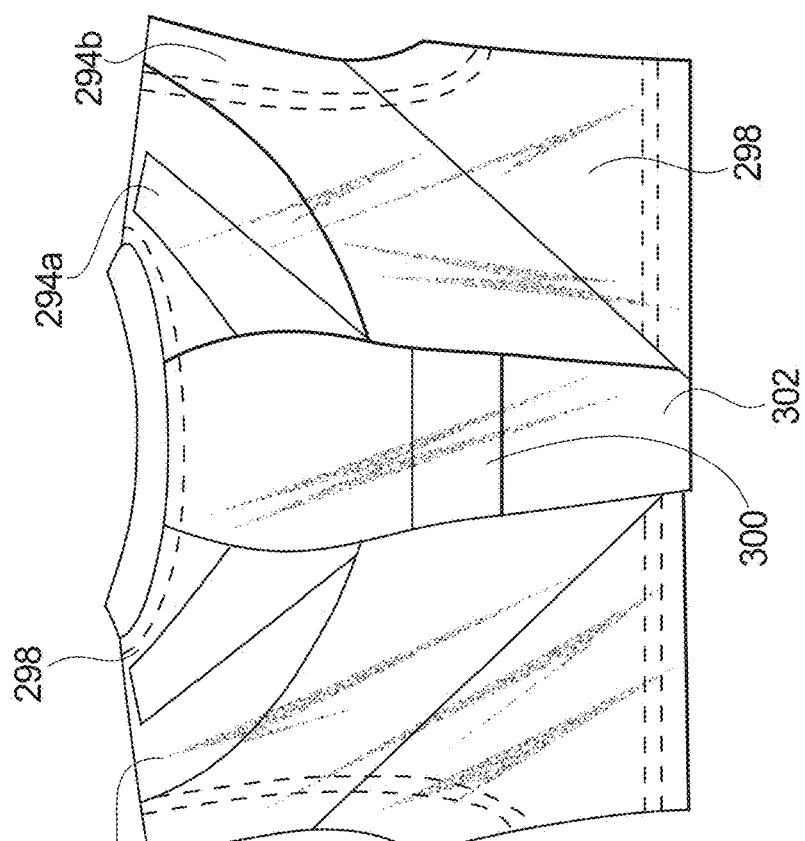
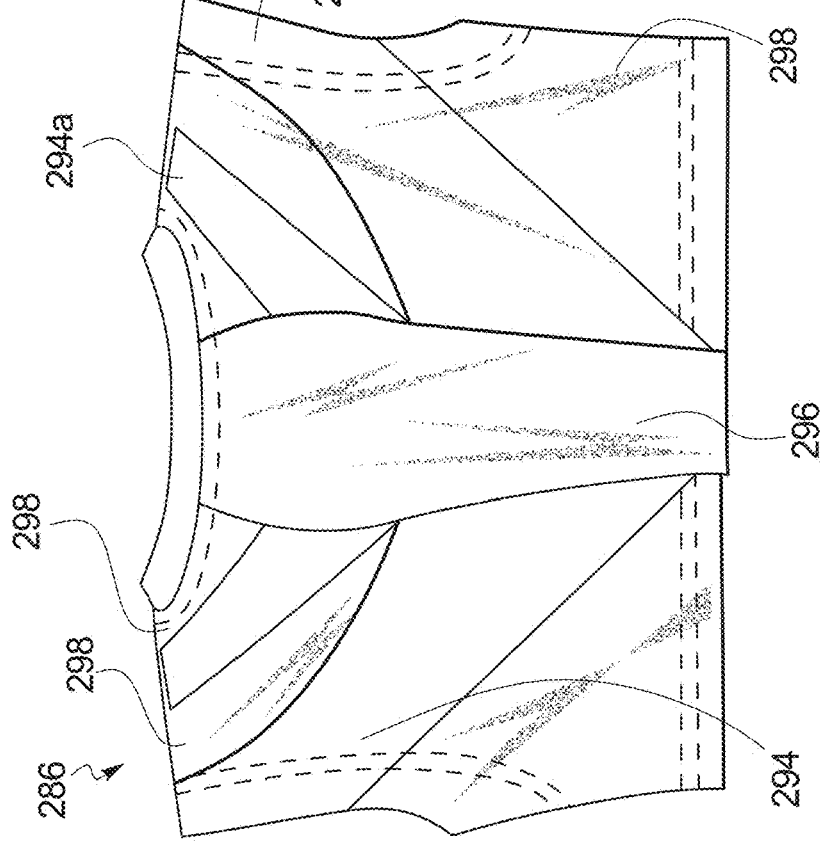

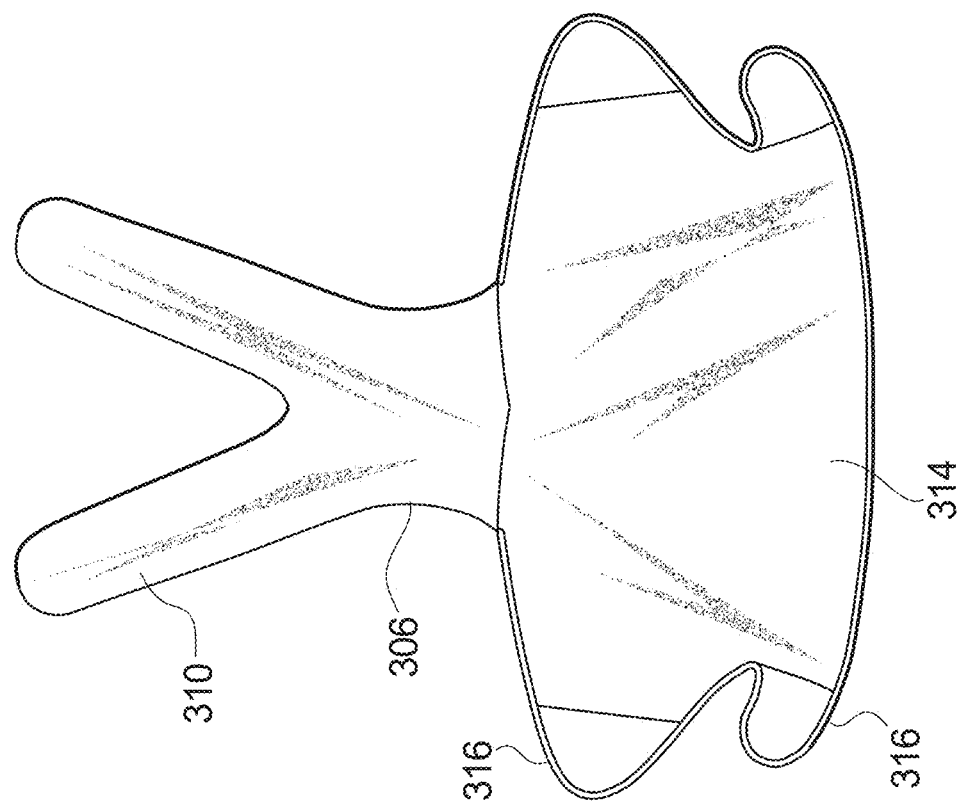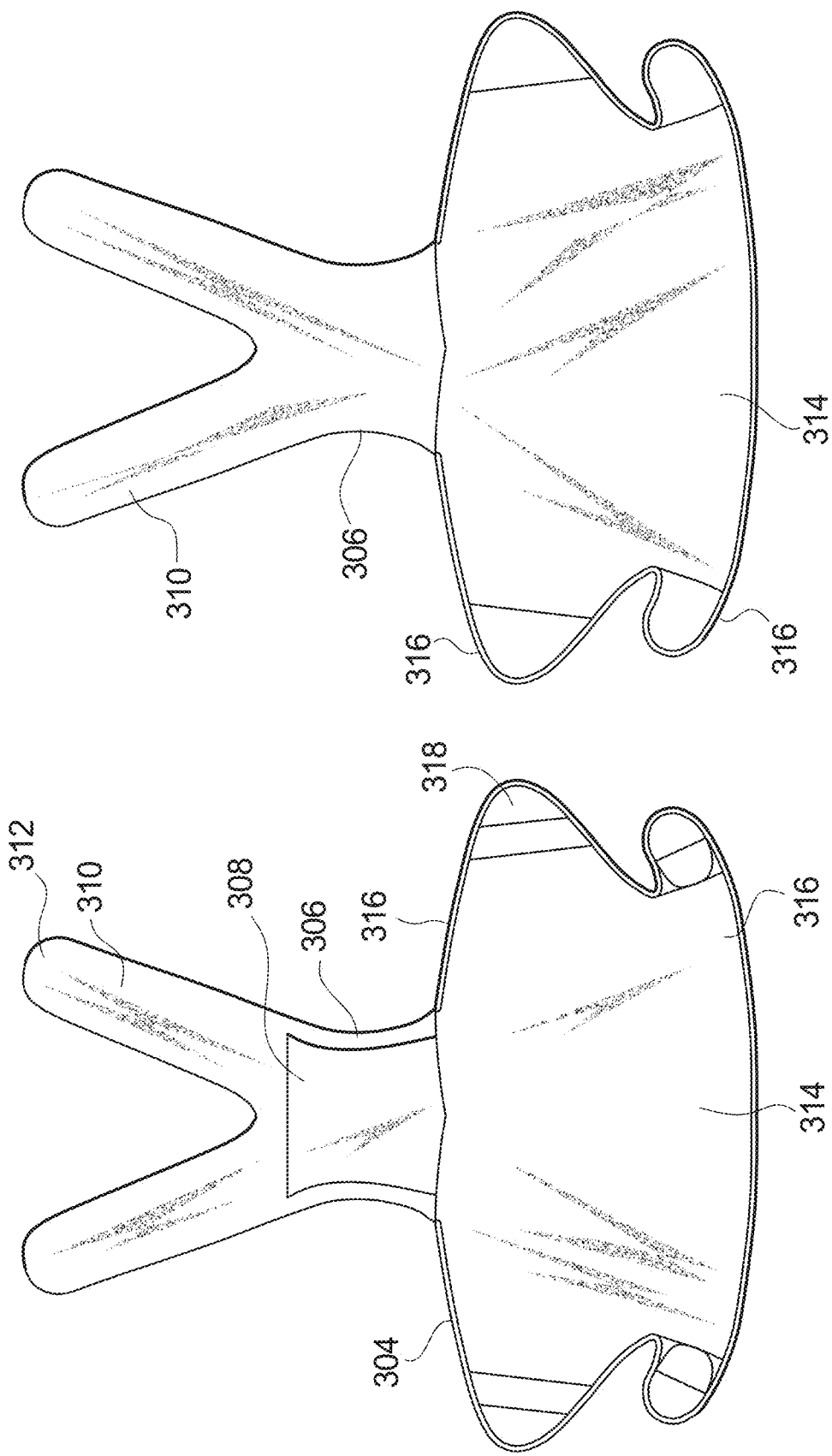

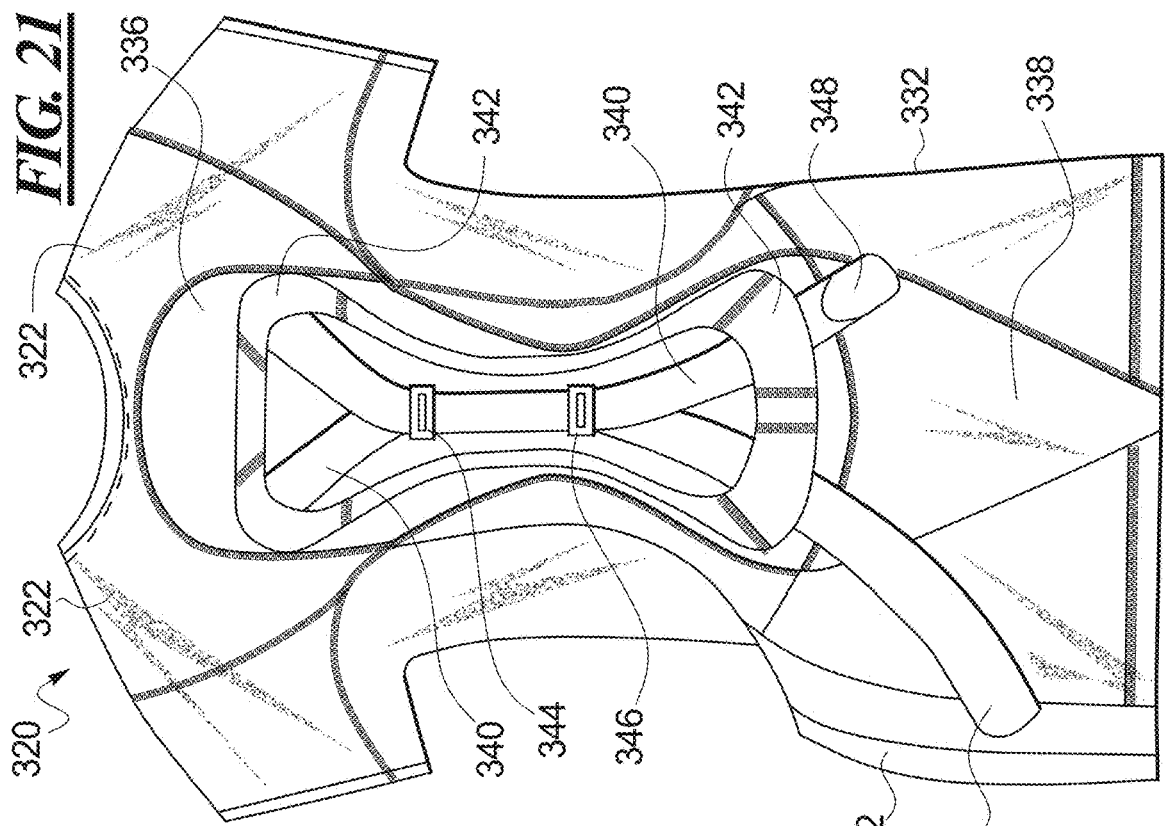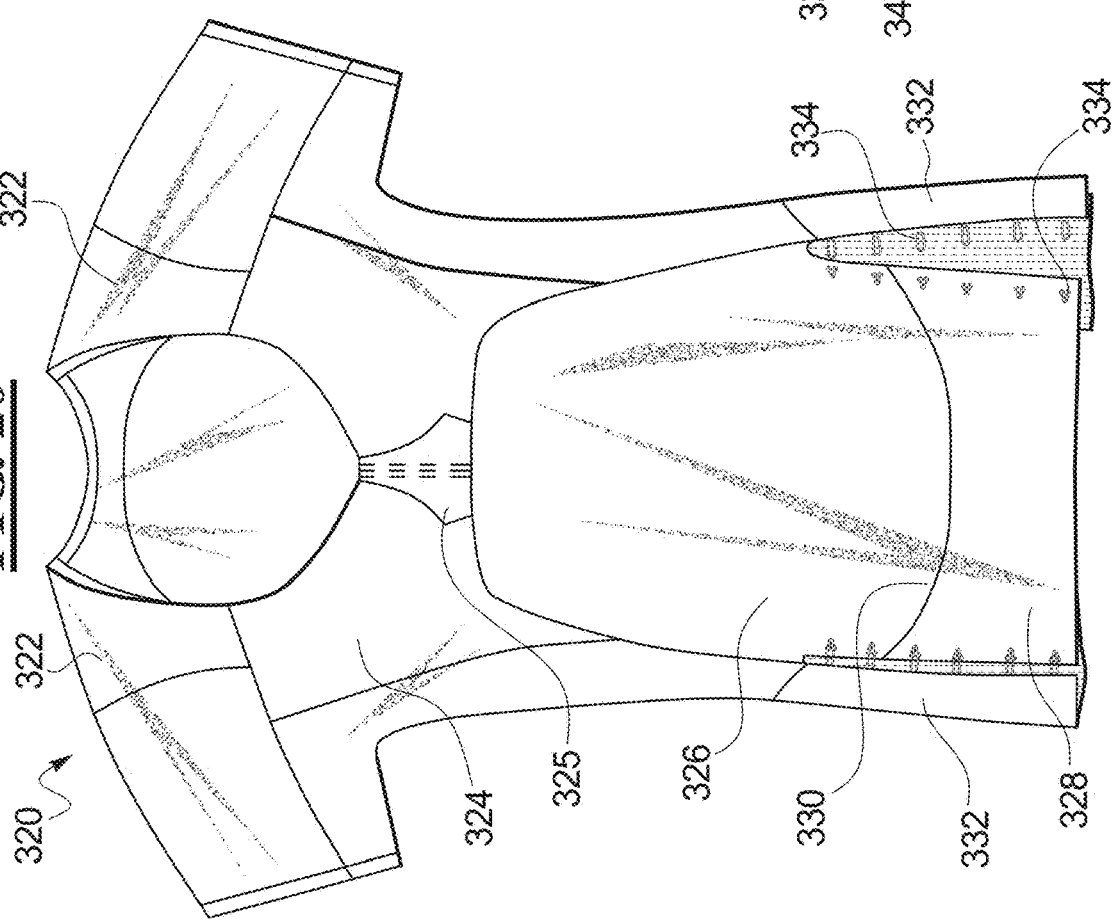

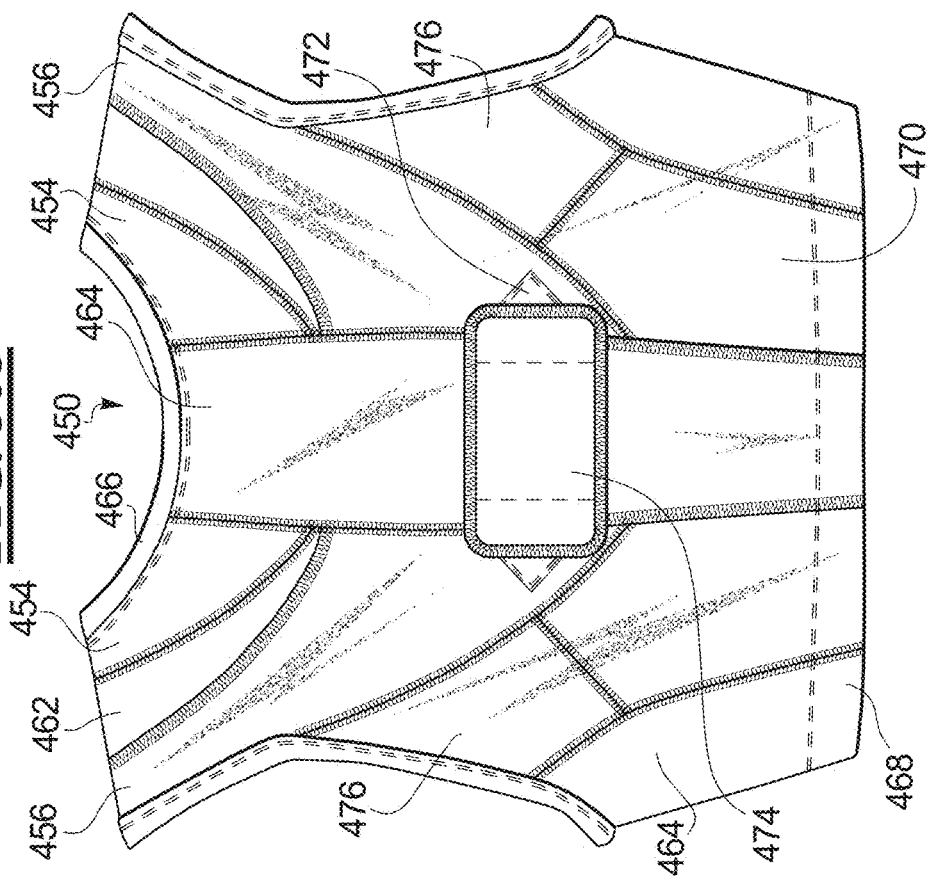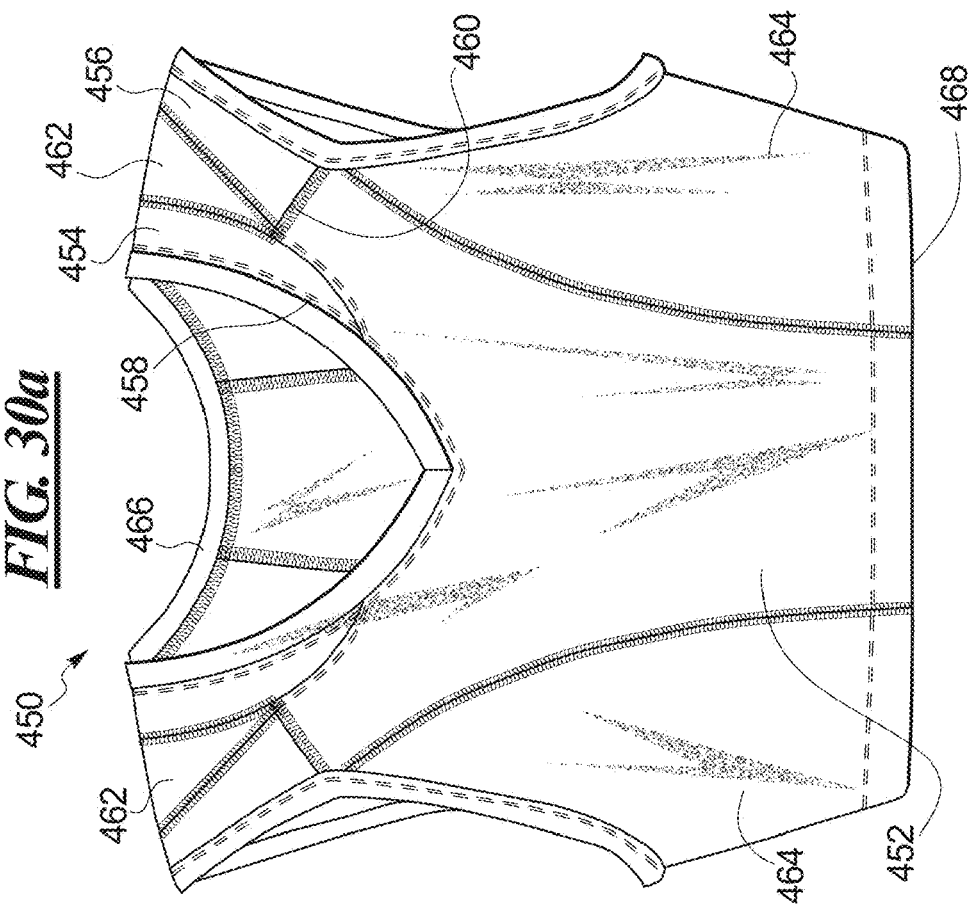

POSTURE CONTROL AND THERAPY SYSTEM

CROSS-REFERENCE TO RELATED APPLICATIONS

This application is a continuation of U.S. patent application Ser. No. 14/455,093, filed Aug. 8, 2014, now U.S. Pat. No. 9,883,703, which claims the benefit of U.S. Provisional Patent Application Ser. No. 61/863,858, filed Aug. 8, 2013, both of which are incorporated herein by reference.

BACKGROUND

The present invention relates generally to a garment or device for wear by a person and in particular to a garment or device having portions for selectively applying tension or other sensory information to the body of the wearer.

Poor posture results from certain muscles tightening up or shortening while others lengthen and become weak which often occurs as a result of one's daily activities. When muscle groups lose balance the body cannot align itself properly. This can lead to distress in the spinal vertebrae and other joints throughout the body. Many physical maladies have been clinically shown to be increased due to prolonged periods of poor posture.

Furthermore, poor posture is becoming more common and worsened by physical stressors that are common to modern activities, such as computer usage, smart phone usage, carrying heavy bags, driving, playing video games, etc., that require prolonged sitting times and abnormal postures that are literally molding our bodies into an abnormal posture profile.

For example, in 2011, the American Academy of Orthopedic Surgery (AAOS) declared "Over 65 percent of upper body injuries, athletic and lifestyle related, come from repetitive overuse and poor posture. Poor posture jeopardizes every sensory path."

Many athletic injuries are the result of poor posture. For example, the Journal of Athletic Training, May 2009 Supplement, states "many overhead athletes suffer from shoulder pain due to poor posture." Overhead athletes are not the only ones at risk. Poor posture injuries can be found everywhere.

The National Institute of Health determined in 2011 that musculoskeletal disorders and diseases are the leading cause of disability in the United States and account for more than one-half of all chronic conditions in people over 50 years of age in developed countries. The economic impact of these conditions is staggering (approximately $890 billion or 7.7% of the Gross Domestic Product), yet they remain under appreciated, under recognized, and under resourced.

BRIEF DESCRIPTION OF THE DRAWINGS

Systems and methods, which embody the various features of the invention, are shown in the enclosed drawings.

FIG. 1a is a front view sleeveless shirt-type garment for improving the posture of the wearer according to a first embodiment;

FIG. 1b is a back view of the sleeveless shirt garment of FIG. 1a;

FIG. 2a is an inside view of the sleeveless shirt garment of FIG. 1a;

FIG. 2b is a side panel of the sleeveless shirt garment of FIG. 1a;

FIG. 3a is an exterior view of a cape garment according to a second embodiment;

FIG. 3b is an interior view of a cape garment of FIG. 3a;

FIG. 4 is a front view of a short sleeved shirt garment according to a third embodiment, showing a lower portion in exploded view;

FIG. 5 is a back view of the short sleeved shirt garment of FIG. 4, showing selected straps in exploded view;

FIG. 6 is a back view of a short sleeved shirt garment of FIG. 4 according to a first variation of the third embodiment, showing a shoulder strap in exploded view;

FIG. 7 is a front view of a shorts garment according to a fourth embodiment;

FIG. 8 is a back view of the shorts garment of FIG. 7;

FIG. 9 is a right side view of the shorts garment of FIG. 7;

FIG. 10 is a left side view of the shorts garment of FIG. 7;

FIG. 11a is a front view and FIG. 11b is a back view of a short sleeved garment for a woman according to a fifth embodiment;

FIG. 12 is a back view of an alternative embodiment the short sleeved garment of FIG. 11, showing selected straps in exploded view;

FIG. 18a is a back view of the crop top or bra top of FIG. 17;

FIG. 18b is a back view of an alternative embodiment of the crop top or bra top of FIG. 17;

FIGS. 19a and 19b are front and rear views of a further embodiment of a cape;

FIG. 20 is a front view of a shirt garment for maternity wear;

FIG. 21 is a back view of the maternity wear garment of FIG. 20, showing a strap in exploded view;

FIGS. 30a and 30b are front and back views, respectively, of an alternative version of the crop top or bra top.

DETAILED DESCRIPTION

Figure 14:
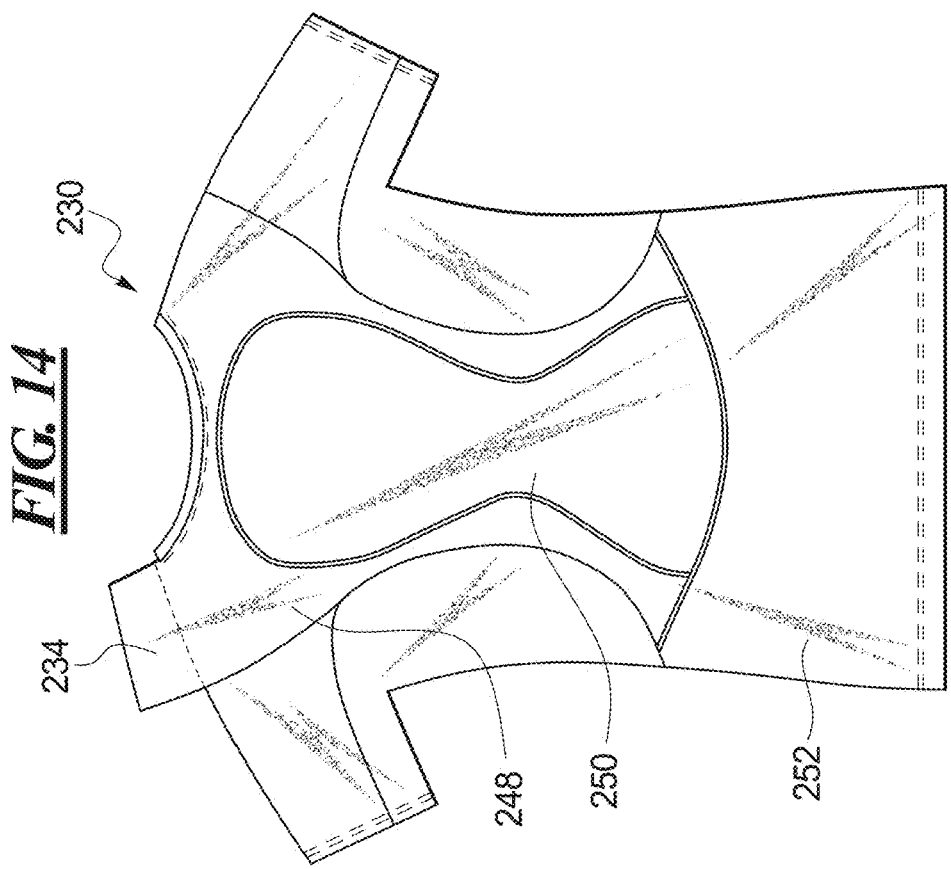
FIG. 14 is a back view of the embodiment of FIG. 13, showing selected straps in exploded view.

Referring first to FIG. 1a, a garment 50 for supporting and activating muscle through tension and elasticity. The garment 50 is in the form of a sleeveless top or shirt includes a front 52 with a closure 54 that includes a zipper to join a right front 56 to a left front 58. The illustrated garment is configured for wear by a man, but variations in proportions and sizes may be made to provide the garment for women, youths and children, for this and all garments disclosed herein. A lower portion 60 of the front 52 is reinforced with a double layer of fabric and includes stitching in a symmetric pattern to join the double fabric layers to one another. The lower portion 60 includes a second closure 62 that includes a plurality of hook and eye fasteners sewn to the adjoining edges of the lower portion at spaced intervals. The hook and eye fasteners of the second closure 62 are located beneath or inside of the zipper closure 54 and are fastened to one another prior to zipping the zipper 54.

The left and right front 56 and 58 includes horizontal stitching 64 extending across the mid to upper chest area of the wearer. Two stitching bands 64 are included in the illustrated embodiment. The left and right front 56 and 58 also include reinforced slits 66 through which extend straps 68. The straps 68 each have a fastener 70 on their free ends. The fasteners 70 are hook portions of hook and loop fasteners, such as Velcro. The garment 50 has a neck band 72 at a neck opening and reinforcing stitching 74 at the arm openings of this sleeveless garment. The tops of the shoulders including the ends of bands 76.

The materials of the garment 50 includes a heavy fabric such as a Lycra blend for the front 52 to which the hook fastener 70 attaches. The neck band 72 is a thinner, stretchier fabric than the body of the front 52. The inner layer of the lower portion 60 is a heavy fabric that resists stretching. The straps 68 are three inch wide elastic bands in certain embodiments.

In FIG. 1b, the back 78 includes bands 76 of a heavier, stretch resistant material that is joined to a back body material 80 of a thinner, stretchier mesh-like material. The bands 76 include a center band 82 that extends along the center of the back 78. The center band 82 extends from the neck band 72 and gradually widens at an upper middle of the back 78, below which a gradual taper narrows the center band 82. The bands 76 also include first and second side bands 84 and 86. The first side band 84 extends from an upper portion of the center band 82 to an inner portion of the shoulder. The second band 76 extends from an upper middle portion of the center band 82, generally at its widest extent, to an outer portion of the shoulder and to the upper portion of the arm opening.

The bands 76, which may be referred to as neurobands, apply tension to the wearer's shoulders and back to encourage good posture. The neurobands both support muscles as well activate muscles. The combination of fabrics that make up the garment have different characteristics, including different stretch characteristics, so as to work by tension and elasticity to activate and support the muscles. In certain embodiments, the heavier fabric of the bands 76 holds in body heat compared to the mesh back body material 80 which permits heat to escape. This local heating and cooling relaxes and stimulates muscles and encourages improved posture and body positioning and motion. Seams 88 joining the bands 76 to the back body material 80 in certain embodiments are formed with heavy thread and flat stitched so as to form raised or sensory seams that contact the wearer's body and thereby provide tactile sensations that also encourage good body posture and motion. The bands 76 direct muscle activity and body position to the core of the wearer's body.

A hem band 90 extends across the lower edge of the back 78 and is reinforced by a band of stretch resistant material having a rubberized or other grippy tactile surface on the inside of the garment 50. The hem band 90 reduces the back of the garment riding up during bending or movement by the wearer. The hem band 90 also provides support for the reinforced lower portion 60 of the front 52. The garment 50 of certain embodiments is long enough to extend to about mid-hip of the wearer, to thereby anchor the tension forces applied by the garment to the body core. The illustrated garment is designed for wear by a man. Other versions for women and children are envisioned and within the scope of this specification.

Turning to FIG. 2a, the interior of the garment 50 is seen but with the front and back cut apart at the shoulder for purposes of illustration so that the interior is better revealed. Of course, the shoulder would not be so cut in the garment for wear. The interior of the front 52 has the reinforcing material 92 at the lower portion 60, with its generally parallel stitching to the fabric of the exterior. The hook and eye fasteners of the second closure 62 are provided along the opposing edges of the lower portion 60. A zipper shield strip 94 extends along an interior edge of the closure 54 on either the left front 58 or right front 56 or both.

The horizontal stitching 64 secures an end 96 of each strap 68 to the front 52. A liner 98 covers the end 96 and a first portion 100 of the strap. The liner 98 extends from the top of the front 52 to the top of the back 78. The straps 68 include a second portion 102 fastened to the first portion 100 where the straps extend out of the liner 98. The straps 68 extend from the front of the upper chest of the wearer, over the shoulders, and cross inside the back 78 before extending out of the reinforced slits 66. By fastening the fasteners 70 at the free ends of the straps 68 to the exterior of the front 52, the wearer applies elastic tension that crosses at the upper portion of the wearer's back to encourage the wearer to hold his or her shoulders back, preventing slouching and encouraging good posture. The wearer is able to control the amount of tension applied by selecting were to affix the straps. The entire exterior of the front 52 may be capable of receiving the fasteners 70 so that the wearer is free to select any desired fastening location. The hem band 90 is seen at the lower edge of the back 78.

In FIG. 2b, the interior of the left front 58 is shown with the liner 98 raised to reveal the first portion 100 of the strap 68 that is positioned under the liner. The strap 68 is secured only at the end 96 at the horizontal stitching 64 and by the fastener 70 at the free end, but is otherwise free to stretch or move within the space formed by the liner 98 and the exterior fabric panels of the garment 50. The horizontal stitching 64 secures a reinforcing band 104 across the interior of the front 52 to which the end 96 of the strap 68 is fastened.

The illustrated garment 50 may be worn by a wearer to encourage good posture and good body position and motion. The garment 50 may be worn directly on the wearer's skin or over another garment. The garment 50 may be worn at the instruction of a doctor or other medical professional, or for physical therapy reasons, or rehabilitation, or may be chosen to be worn by the wearer for other reasons. If the effect on the wearer's posture and body position is not sufficient from the garment 50 alone, a supplemental garment may be provided. One such supplemental garment may include elastic bands that fasten to the fabric of the front at the upper portion of the exterior surface, extend crossed over the back and are fastened to the front at the lower portion. In some instances, the additional elastic bands may follow the same path as the bands 68 within the garment 50. The crossed bands may include a support where the bands cross of the type provided for suspenders, for example.

Additional garments are provided by may form a system of garments that may be worn separately or together to obtain the desired results. One such additional garment is a further supplemental support 106 is shown in FIG. 3a. The supplemental support 106 may be referred to as a cape. The exterior of the cape or support 106 has a center portion 108 from which extend two shoulder straps 110. The opposite end of the cape 106 has a lower back support 112 with one or two laterally extending portions 114. The center portion 108 includes a double layer of fabric with an opening 116 of a pocket 118 formed by the double layer. The pocket 118 may be selectively closed for example by a hook and loop fastener 120 within the inside of the opening to permit the wearer to selectively open or close the pocket 118. A heat pack cold pack or other thermal or therapeutic device may be positioned within the pocket, for example when the cape 106 is worn.

FIG. 3b shows the interior surface of the cape 106. The shoulder straps 110 each have a fastener 120 at the free end. The fasteners 120 of certain embodiments are hook portions of hook and loop fasteners that may be attached, for example, to the front 52 of the garment 50 so that the shoulder straps extend from the front of the garment 50 and over the wearer's shoulders. This positions the center portion 108 at the center of the wearer's back. The cape 106 has the laterally extending portions 114 that also have fasteners 122 at the free end. The fasteners 122 may fasten to a garment worn by the wearer, for example, to the garment 50. The fasteners 122 affix to the lower portion 60 of the garment 50, for example. Tension is applied around the core by the lower back support 112 and to urge the shoulders back by the shoulder straps 110. The cape 106 may be a supplement to the garment 50 or may be used alone, so long as the wearer is wearing a garment to which the fasteners 120 and 122 may be attached. An additional pocket or other feature 124 may be provided on the inside surface.

A further embodiment that may be included in the system is shown in FIG. 4 wherein a short sleeved shirt garment 126. The shirt includes a front 128 with a center panel 130 that extends from a neck band 132 to a bottom hem 134. A flap 136 in certain embodiments is a continuous part of the center panel 130 that is shown extending below the bottom hem 134 but which will be folded at the bottom hem 134 to form a double walled lower section 138. The center panel 130 is of a stretchy fabric that applies tension to the wearer, and the double thickness at the lower section 138 applies additional tension and compressive pressure at the lower portion of the wearer's torso, bringing forces back to the wearer's core.

The front 128 also has portions of side panels 140 that are sewn to the center panel and that also form undersides of sleeves 142. Top portions 144 of the sleeves 142 extend from the ends of the sleeves 142 to shoulder straps 146. The shoulder straps 146 extend from the tops 144 of the sleeves to the neck band 132. A strip 148 is affixed between an end of each shoulder strap 146 and the center panel 140, the strips 148 extending diagonally from the neck band 132. In certain embodiments, the strips 148 are formed of loop portions of a hook and loop fastener so that hook portions of the fastener may be attached at the strips 148. Similar strips are provided in many of the garments in this system. Side straps 150 extend around the sides of the garment 126 and affix to opposite sides of the double walled lower section 138. The side straps 150 may include loop portions of a hook and loop fastener to provide a landing pad or connection site for hoop portions of the fastener to attach. Similar loop portions may be provided on other embodiments in this system.

FIG. 5 shows the shirt garment 126 of FIG. 4, also called a posture shirt, from the back. The back includes a core portion 152 of a first fabric that is overlaid on or stitched into a corresponding opening in a strap panel 154. The core portion 152 of the illustrated embodiment has a generally hourglass shape with a wider portion at the upper back and a second wider portion at the lower back. The core portion 152 may be of stretch resistant material that may also hold in heat to apply both tension and heat to the core of the wearer. The strap panel 154 has two shoulder straps 146 that extend over the shoulders of the shirt so as to apply tension to the shoulders of the wearer. One of the shoulder straps 146 is shown cut away from the front of the shirt for purposes of illustrating the length and configuration of the shirt. A lower back panel 156 extends across the lower back of the shirt 126 and connects to both the core portion 152 and the strap panel 154. The lower back panel 156 may be of a relatively low stretch fabric and may be separate from the core portion 152 and strap panel 154 and joined thereto by sewn seams, for example, or may be formed in one piece with one or more of the core portion 152 and the strap panel 154. The lower back panel 156 has sidewardly extending portions that form the side straps 150 which are attached at the double thickness lower section 138 of the front. One of the side straps 150 is shown cut from the shirt for purposes of illustration. The side panels 140 and top portions 144 of the sleeves 142 extend from the front as well.

The core portion 152 and shoulder and side straps 146 and 150 are formed of fabrics that applies tension during movement and while the wearer is still. Tactile sensations from the straps and seams as well as retained heat over selective area encourage muscle and tissue relaxation to further improve posture and motion.

FIG. 6 is a back view of an alternative shirt 158 that includes a lower back panel 160 of a same fabric as the body of the shirt. The lower back panel 160 may instead be of a different fabric than the shirt body. The core portion 152 and strap panel 154 are similar or identical to the embodiment of FIG. 5.

FIG. 7 is an illustration of a pair of shorts type garment 162, shown from the front, that uses bands, also referred to as neurobands, to apply tension to muscles and tissue areas of the body and to activate muscles, similar to the vest, cape and shirt described above. The shorts may be part of the system. In addition to the illustrated shorts, longer pants may be provided. The neurobands on the shorts transfer forces to the body core. In particular, the embodiment of the shorts 162 includes a body 164 to which are provided bands or straps 164. The straps 164 include a waist strap 166 that is releasable at both opposite ends. The waist strap ends each have a fastener 168 that affixes to a central panel 170. The fastener 168 is one portion of a hook and loop fastener and the central panel 170 is the other portion. The central panel 170 is covered by a flexible cover 172 in certain embodiments. The cover 172, also referred to as a pouch, prevents accidental release of the waist strap fastener 168 yet is flexible enough that the wearer may reach under the cover to attach or release the waist strap fastener 168. The wearer may instead affix the ends of the straps 168 and 174 to the outside of the cover or pouch 172, or may even stretch the straps to affix the ends of the straps to the body of the shorts with the straps across the cover or pouch 172, depending on wearer preference. The straps are of elastic bands or UVL.

A hip strap 174 is positioned below the waist strap 166. The hip strap 174 has two free ends that include fasteners 176 that may be attached to the central panel 170 in the same way as the waist strap ends. One side of the waist strap and hip strap is shown released and one side is shown affixed in this view. The shorts 162 include spiral strap portions 178 in this view. A crotch panel 180 is provided.

In FIG. 8 can be seen that the waist strap 166 and hip strap 174 of the shorts 162 extend from a central lower back panel 182. The lower back panel 182, as seen from the back, extends below the waist strap 166 and the hip strap 174 and contact the spiral strap portions 178. Tension applied by the straps at the waist and hips is communicated to the spiral wrapped straps 178. The straps 178 extend in a helical inclined about the leg of the shorts 162 to hems 184 of the legs 186. Tension is applied in a spiral direction to the legs and lower torso of the wearer by the straps. The spiral straps may also be releasable to selectively control tension on the straps by the wearer. Fastening sites 188 are stitched to the back of the legs 186. The fastening sites 188 may receive hook portions of hook and loop fasteners of additional straps that the user may wish to wear. The fastening sites are formed as loops, such as belt loop-type structures, so that straps may be affixed to the shorts through the loops. The shorts apply tension that is drawn toward the body core of the wearer, improving motion and posture.

A side view of the shorts 162 is shown in FIG. 9. Tensions applied by the spiral straps 178 are indicated by arrows B. Tensions are controlled by the wearer via selective tension applied to the straps 166 and 174 as they are affixed to the central panel 170. The straps 166 and 174 are free of the body of the shorts 162 except where stitched at 190 along the back of the waist band and at 192 and 194 along the edges of the central lower back panel. Tension is applied to the wearer's core. A diamond shaped element 196 is provided on the upper side of the shorts 162.

In the view of FIG. 10, the shorts 162 has the straps 166 and 174 released, revealing that the sides of the shorts may be opened at 198. Affixing the straps 166 and 174 to the central panel 170 closes the sides of the shorts 162. The element 196 may be a fastener, fastening site, or loop to which to attach additional spiral straps that may be wrapped about the legs 186 and affixed at the fastening sites 188.

Figure 31:
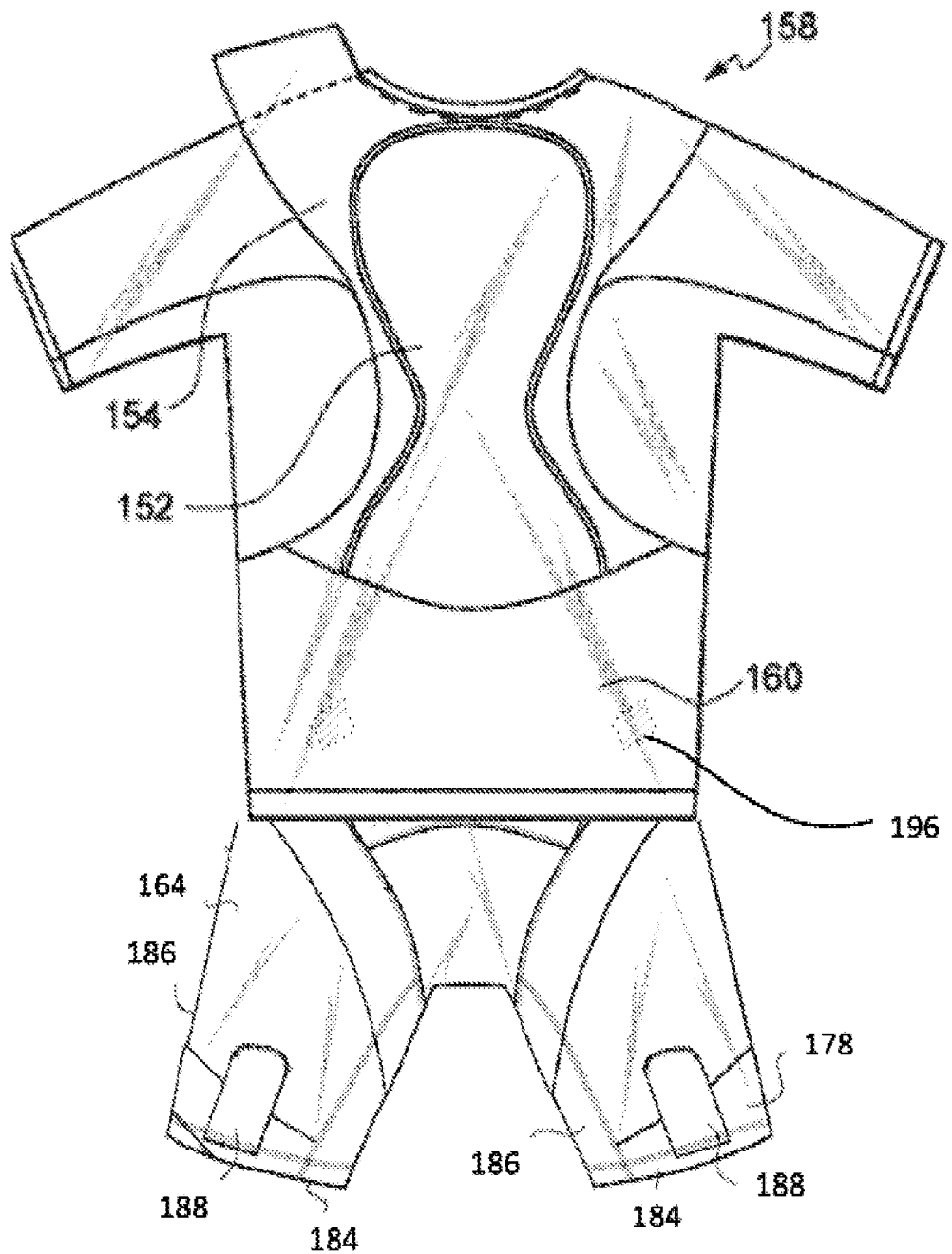
FIG. 31 is a back view of a system including an exemplary short of FIG. 8 and short sleeve shirt of FIG. 6 used in combination.

FIG. 31 is an exemplary back view of a system according to embodiments described herein including an exemplary short of FIG. 8 and short sleeve shirt of FIG. 6 used in combination. The element 196, although covered by short sleeve shirt, is illustrated for purposes of showing an exemplary fastener, fastening site, or loop to which the garments may be attached. There may be a first and second element 196, which may be a hip fastener site, located between the central lower back panel and the front center panel.

The garments show so far may be worn by men, women or children, although the illustrated examples are designed for wear by men. In FIG. 11a is a pullover woman's version 200 of the shirt of FIG. 4. The construction and materials are the same or similar except that the woman's version includes a somewhat different contour for the upper torso on the center panel 202. Stitching 204 and possible other reinforcement or support is provided to accommodate a woman's bustline. The stitching may be eliminated in some embodiments. The lower portion of the shirt 200 including the double layer lower section 206 and the side straps 208 may be wider as well. The shoulder straps 210 and diagonal strips 212 are generally the same as the version described above.

In the back view of FIG. 11b of the woman's version, the strap panel 214 has the shoulder straps 210 and connects to the side straps 208. The core portion 216 is at the center of the back in an hourglass shape. The embodiment shown here includes an additional curved shoulder band 218 that extends from side to side of the upper portion of the core portion 216 to apply added tension across the upper back of the wearer. The curved band 218 of certain embodiments may be the loop portion of a hook and loop fastener to which may be attached short bands to apply additional tension at the back, referred to as scapula tension. The short bands will be described later herein.

FIG. 12 is an alternative embodiment of a posture shirt 220 for a woman or for a child, shown from the back. An hourglass shaped core portion 222 is sewn onto or otherwise affixed to the strap panel 224 which has shoulder straps 226 and side straps 228. A supplemental upper back strap 229 is provided across the upper portion of the hourglass shaped core portion 222. Further descriptions of the features are not provided for the sake of brevity.

Figure 13:
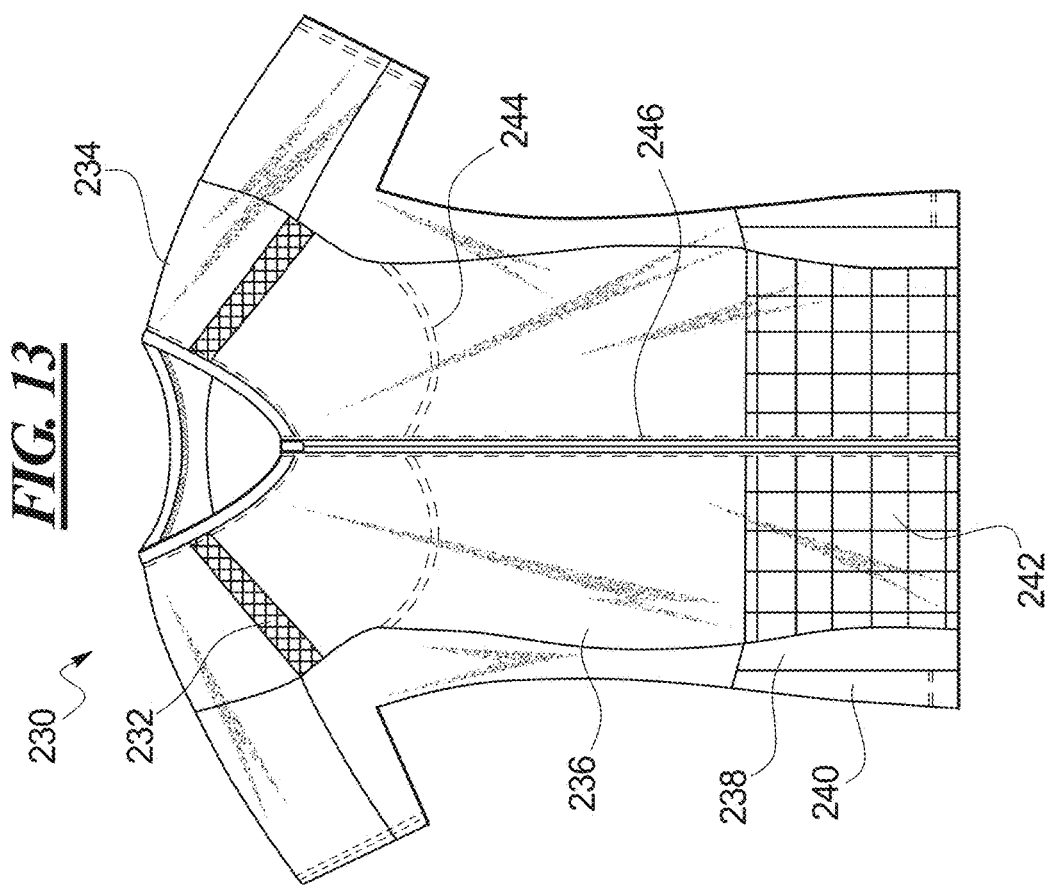
FIG. 13 is a front view of a zipper front short sleeved woman's shirt of a further embodiment.

FIG. 13 shows an embodiment of a woman's version of the posture shirt 230 that has the diagonal strips 232 connecting the shoulder straps 234 to the central panel 236. The diagonal strips may be loop portions of a hook and loop fastener. An additional strip 238 is connected between the side straps 240 and the reinforced lower portion 242 of the central panel 236. The additional strip 238 may also be loop portions of a hook and loop fastener. The stitching 244 is provided to accommodate a woman's figure. The version of the shirt 230 shown here has a front closure 246, such as a zipper or other fastener. The shirt 230 may be a pull over or partial zip shirt as well. Similarly, the pull over shirts shown herein may be provided with a front closure or other closure.

FIG. 14 shows that the zipper closure shirt 230 has the strap panel 248 and core portion 250. The side straps 252 may be of the same material or a different material from the strap panel 248.

Figure 15:
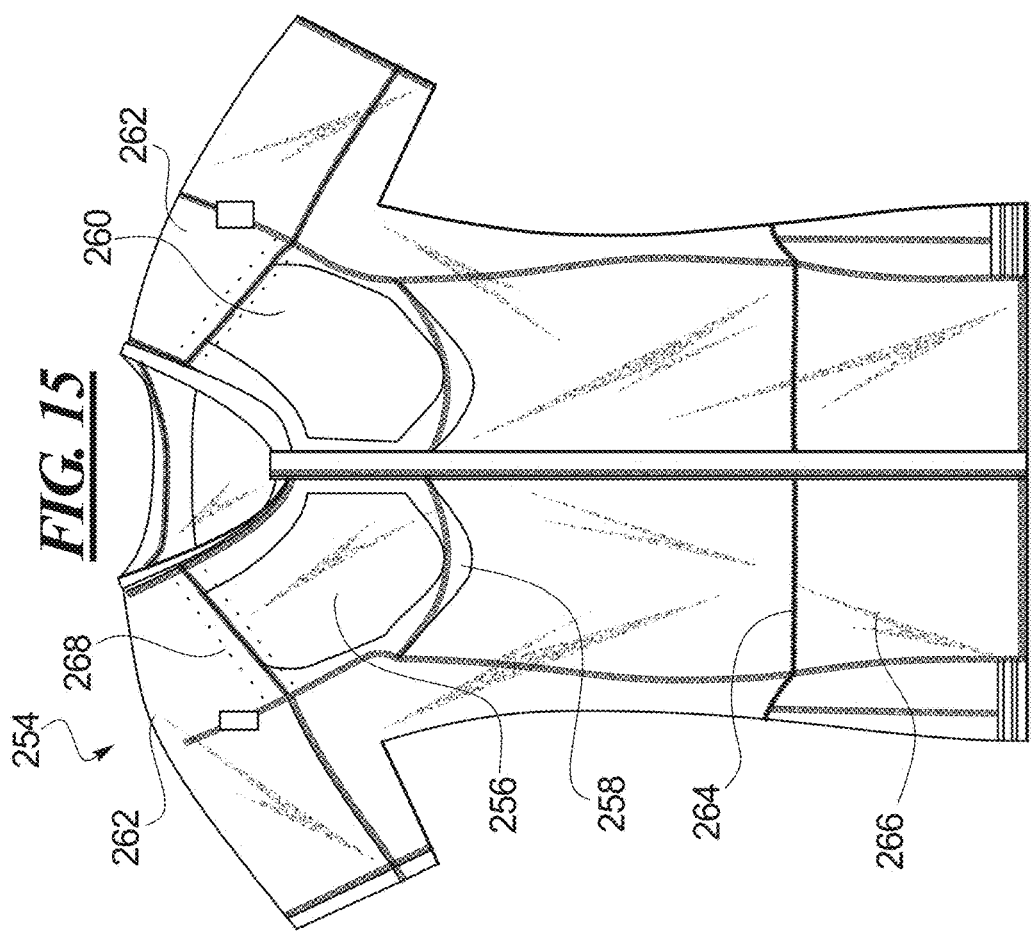
FIG. 15 is an internal of the woman's garment of FIG. 13.

In FIG. 15, a woman's version of the zippered short sleeve shirt 254 has a bra section 256 that includes a first portion 258 over the bust area of the wearer. The first portion 258 may be of a foam-type material. The internal structure of the shirt 254 is shown with the shirt turned inside-out. Second bust portions 260 are on the inside of the first portion. The first portion 258 and the second bust portions 260 extend to the shoulder straps 262 that extend over the shoulders from the strap panel. The stitching 264 for the double thickness lower portion 266 can be seen in this inside out view. Stitching 268 for the diagonals at the neck area show that the diagonals secure the shoulder straps 262 to the bust portions 260.

Figure 16A:
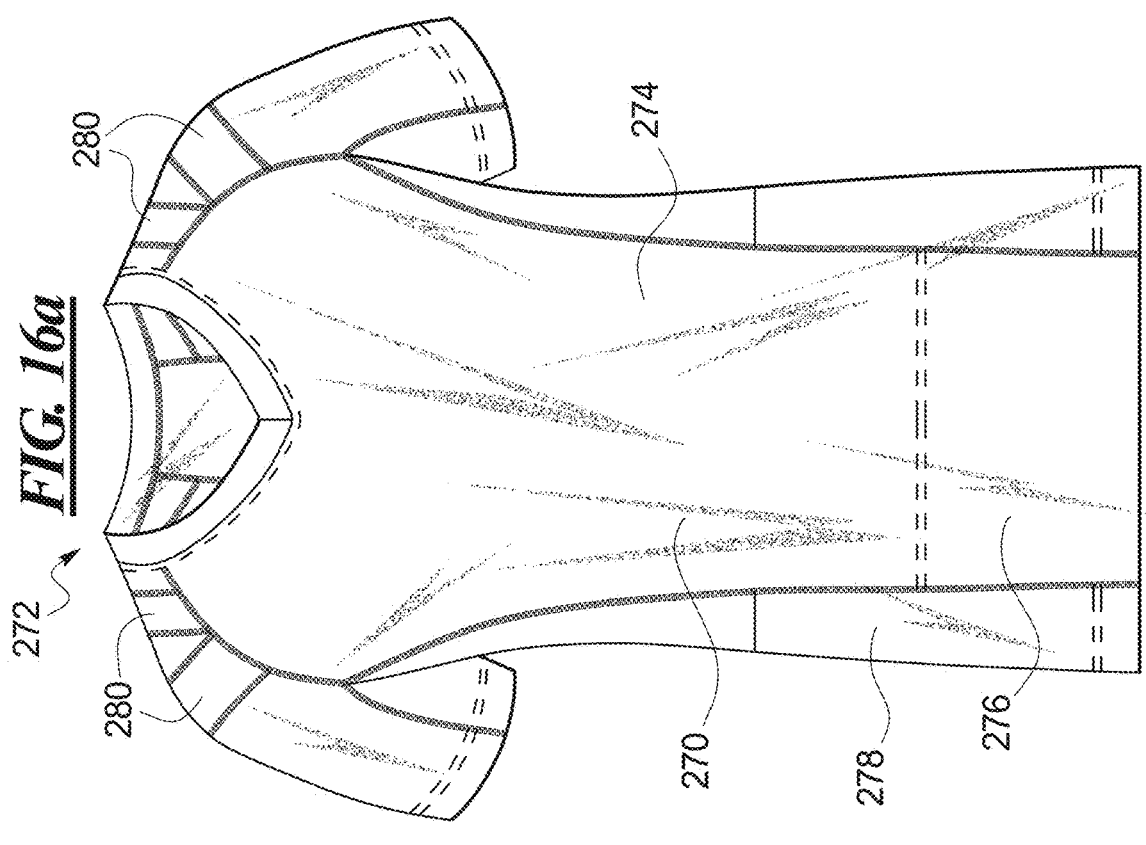
FIGS. 16a and 16b are front and back views, respectively, of an embodiment of a posture promoting shirt for men, for example.

FIG. 16a shows a front 270 of a short sleeved shirt 272 that includes a central panel 274 with a reinforced lower portion 276. Wider side straps 278 are provided connected to the lower portion 276 and extending up the side panel of the shirt 272. The side straps 278 are of a rib knit fabric, for example to which hook portions of a hook and loop fastener may be affixed. Two pairs of shoulder straps 280 extend over the shoulder to the central panel 274.

Figure 16B:
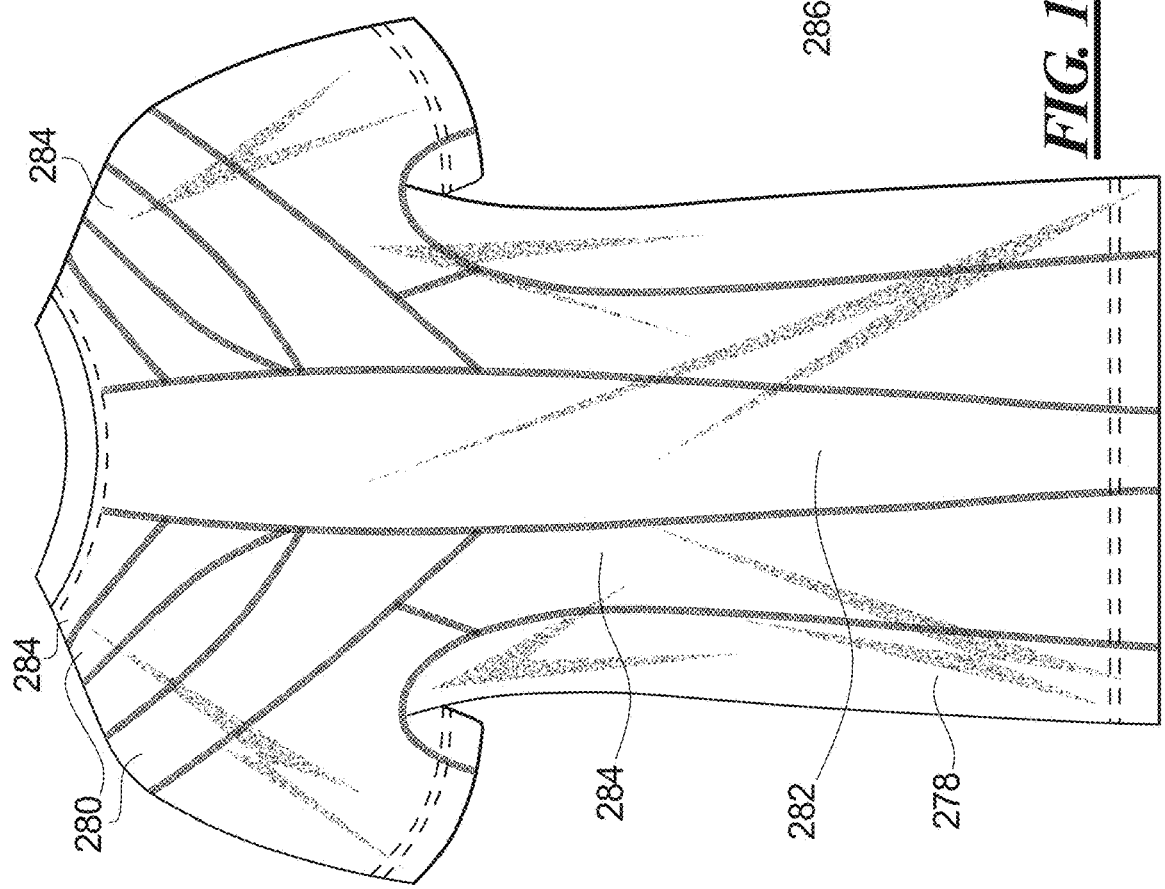

The back view of FIG. 16b shows that the shirt 272 has a center band 282 and paired diagonal shoulder straps 280 extending from a core direction over the shoulders. The shoulder straps 280 and center band 282 of certain embodiments are of French terry material that is resistant to stretching and provides a heat insulating property, for example. Mesh fabric 284 connected to the straps 280 and center band 282 provides stretchy, non-tension applying fabric that permits cooling of the body portions under the mesh. Two such mesh sections 284 are provided at the shoulder straps 280 and another mesh section is provided at either side of the center band 282. Tension and heat are thereby concentrated on the areas under the straps and center band to encourage posture. Elastic movement and release of body heat are provided by the mesh panels. The front, upper side panels and sleeves are of poly-lycra. The tactile different between the fabrics, as well as raised stitching at the seams connecting the fabrics provides biofeedback to the wearer to further improve posture.

Figure 17:
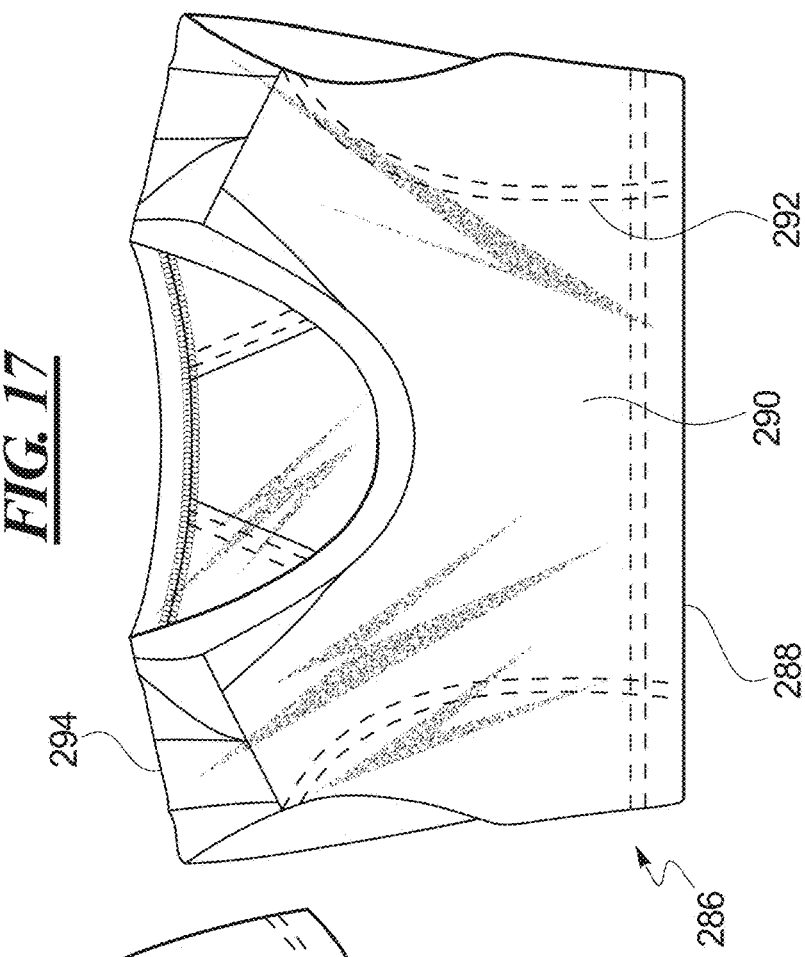
FIG. 17 is a front view of a crop top or bra top for women according to another embodiment.

Turning to FIG. 17, the same principles as described herein may be applied to a crop top or bra top 286 for wear by a woman, such as during exercise. The top 286 has a shortened hem 288, a front panel 290 with side stitching 292, and shoulder straps 294. In FIG. 18a the top 286 has the center band 296 that connects to the diagonal paired shoulder straps 294. The shoulder straps 294 and center band 296 are of tension resistant material such as French terry that stretches less than body material 298, for example, mesh, that is between the bands and straps, so that tension is selectively applied to encourage improved posture. Two mesh panels 298 are provided at the shoulder straps 294 and one mesh panel or poly-lycra panel at each side of the center band 296.

FIG. 18b shows a similar top back view to FIG. 18a but with an added tension strap 300 in the center band 302. The tension strap 300 may receive an add-on scapula strap, for example, and may be formed of a loop portion of a hook and loop fastener. Both embodiments of FIGS. 18a and 18b have the center band 296 and 302 at the center of the back but the center band has a different shape than on the longer shirts. In particular, the center band has a greater width below the neck band at the upper shoulder strap 294a and tapers to a narrower shape at the lower shoulder strap 294b.

FIGS. 19a and 19b show a cape 304 that may be used for women or children for additional posture support. The cape 304 includes a body 306 with a pocket 308 for holding a heating or cooling pack or other therapeutic item. The shoulder straps 310 are shorter for children but may be longer for use by women and include fasteners 312 on the free ends. A back panel 314 is provided on the lower end of the body 306, the back panel 314 having two lateral extensions 316 from each side, each with a fastener 318 for fastening to a garment worn by the wearer. The fastener 318 of certain embodiments is a hook fastener of a hook and loop fastener. The wearer may wear a garment that permits the hook fastener to attach to the garment, such as one of the vests or shirts described above, and may affix the cape 304 to the garment for additional posture support.

FIG. 20 shows a maternity top 320 for a woman. The top includes shoulder straps 322 that extend over the shoulders, a bust support area 324 with a center section or spacer 325, an abdominal panel 326 and a lower portion 328. The shoulder straps 322 and spacer 325 of this embodiment, as well as other embodiments disclosed herein, may be of a stiff supporting fabric having a bonding quality. The bonding quality fabric is layer bonded and is relatively rigid and without significant stretch. This type of fabric is used in jackets, for example. The abdominal panel 326 is of stretchy fabric to accommodate the changing shape of the wearer during a pregnancy. The lower portion 328 is of double thickness for core stability and has a curved upper edge 330 for the wearer's abdomen. The lower portion 328 is affixed to side straps 332 by fasteners 334, such as hook and eye fasteners at the two opposite sides of the lower portion 332. The top 320 is short sleeved. It is also foreseen with this and other tops and shirts that the tops and shirts may be sleeveless or long sleeved or of some intermediate sleeve length.

FIG. 21 shows the back of the maternity top 320. The shoulder straps 322 extend from the front to the back as a strap panel. The strap panel includes the side straps 332 that extend at the hips around to the front of the top 320 for fastening to the lower portion 328 using the fasteners 334. On the strap panel 322 is a core portion 336 of a fabric with low stretch characteristics. The core portion 336 has a hourglass shape and includes a tail portion 338 that extends to the lower hem in a tapered shape. For added back support, the top 320 includes straps 340 that provide additional tension and support. The straps 340 form an X shape at the back of the top 320 with upper ends of the straps 340 secured under a retainer strap 342. The straps 340 come together and are held in a first retainer loop 344. The straps 340 remain together and pass through a second retainer loop 346 before separating and extending toward the side straps 332 at the hips. The retainer loops 344 and 346 are adjustable along the length of the straps 340 depending on the wearer's preference. Stitch lines are indicated on the straps 340, which are stitched to hold pieces together. The separated straps 340 pass under another portion of the retainer strap 342. Free ends 348 of the straps 340 include fasteners, such as hook fasteners, that enable the wearer to adjust the positions of the strap ends 348 and thus adjust the tension provided by the straps 340. The fasteners on the strap ends 348 are fastenable to the fabric of the side straps 322, for example. The straps 340 are free to move with the wearer by passing through the retainer loops 344 and 346 and under the lower portion of the retainer strap 342 while providing support to the wearer. The retainer strap 342 is of a hard fabric that provides support to the center of the back of the wearer. Stitch lines are indicated for locations where the retainer strap 342 is sewn to the underlying fabric layers.

Figure 22:
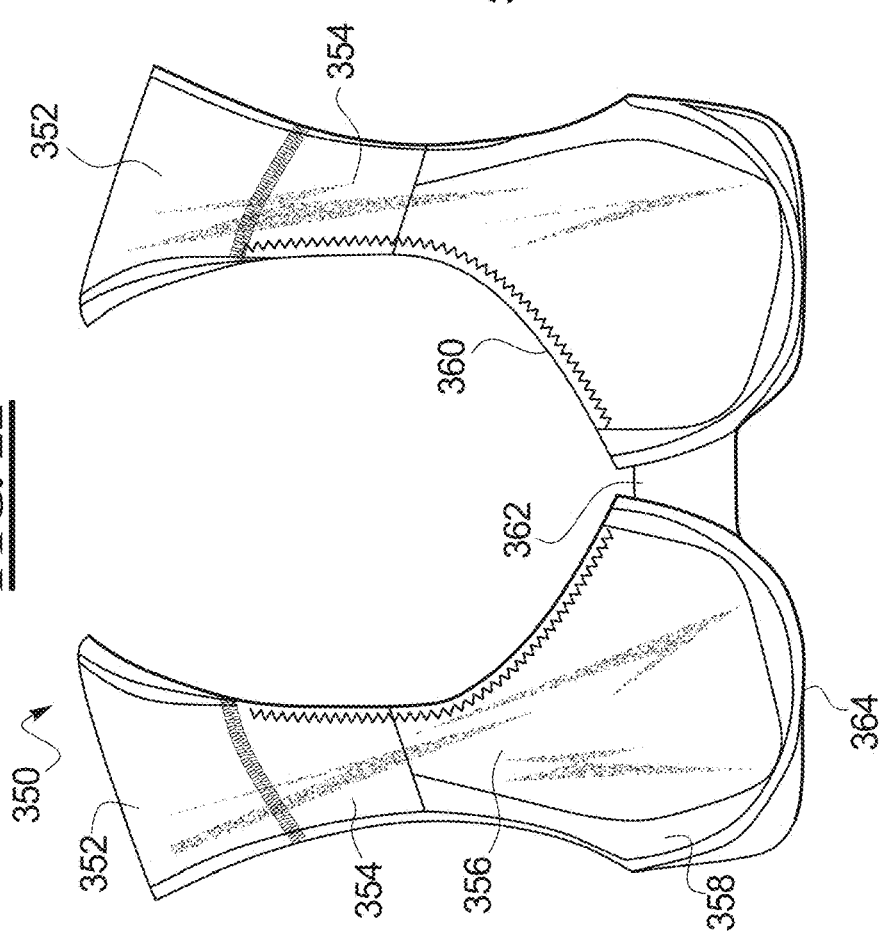
FIG. 22 is a front view of a bra portion of the maternity wear garment of FIG. 20.

FIG. 22 shows a bra portion 350 of the maternity top 320. The bra portion is internal to the maternity top 320 and may be permanently affixed within the top 320 or removable from the top 320. In the preferred embodiment, the bra is sewn into the top. The bra portion 350 may be available in different sizes as needed. The bra portion 350 includes shoulder straps 352 that extend from the back of the top. Upper support sections 354 connect from the shoulder straps 352 to bra cup portions 356. The bra cup portions 356 include generally J-shaped support strips 358 of curved foam pieces that are fastened to the upper support sections 354 and extend around the outside of the cup. Neck line stitching 360 extends from the upper support sections 354 to the inside ends of the support strips 358. A center support 362 is connected between the cups. Underwires 364 are provided as well, which may be of metal wire, plastic or of cord, for example.

Figure 23A:
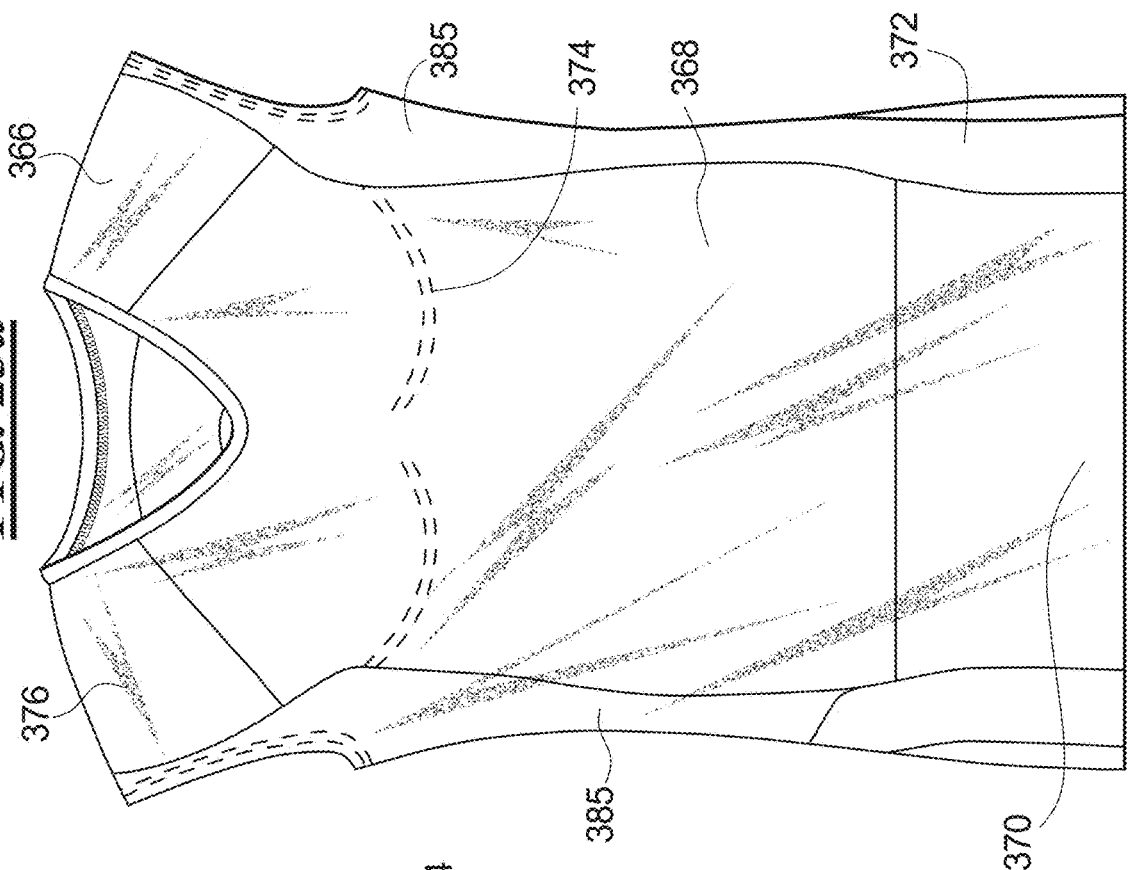
FIGS. 23a and 23b are front and back views, respectively, of a woman's sleeveless pullover garment of a further embodiment, selected straps being shown in exploded view.
Figure 23B:
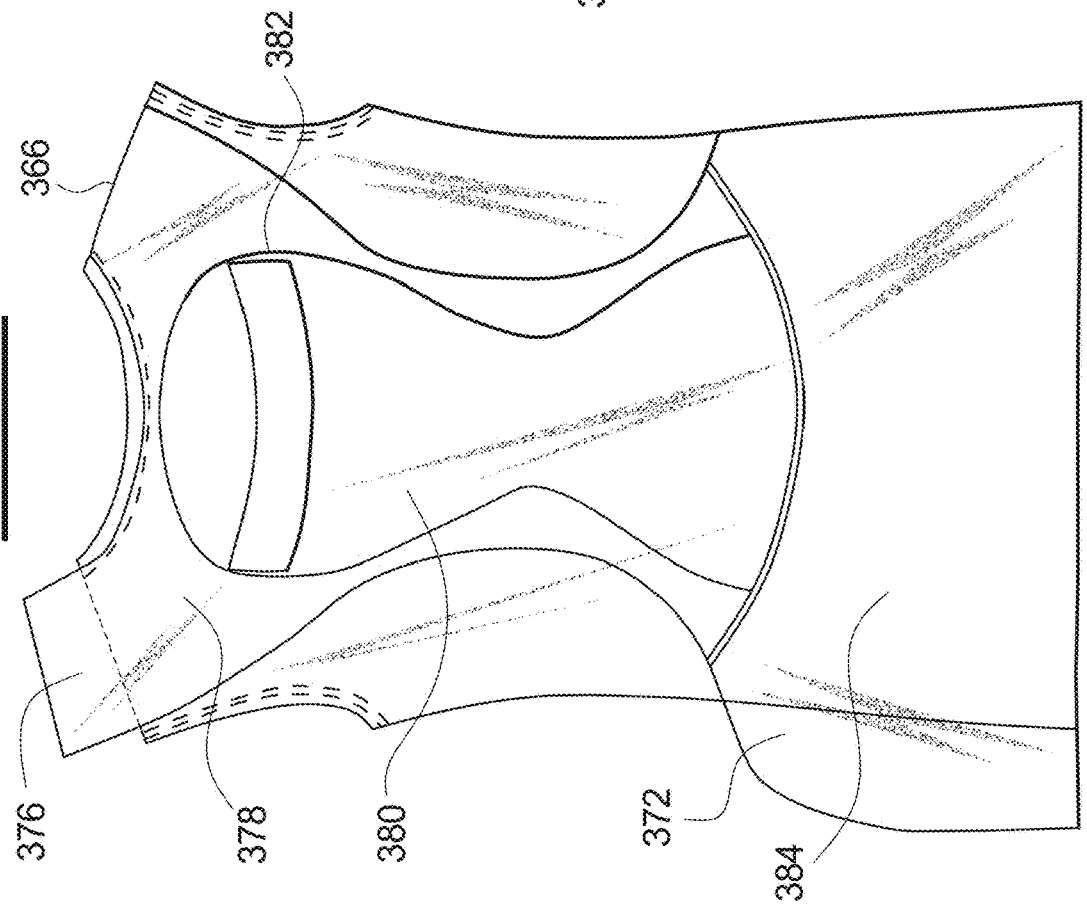

In FIGS. 23a and 23b, a pullover sleeveless shirt garment 366 for women is provided. The sleeveless shirt includes a front panel 368 having a lower portion 370 of doubled fabric connected to sided straps 372. The front panel has bust support stitching 374 that may be attached to an internal bra structure, for example of the type shown herein. Shoulder straps 376 connect the front panel 368 to a strap panel 378 on the back of the shirt 366 that connects between the shoulder straps 376 and the side straps 372. The shoulder straps and side straps may include loop fastener portions for a hook and loop fastener where the straps connect at the front of the garment. An hourglass shaped core portion 380 is affixed to the strap panel 378 at the center of the back for core support. A curved additional band 382, for example of a loop portions of a fastener, extends across the top of the core portion 380. A lower back support 384 may be part of the strap panel 378 or may be overlying the strap panel or may be attached to the strap panel. The lower back support of certain embodiments is spacer fabric. Sides 385 connect the front and back together to form the sleeveless shirt. The side straps 372 and shoulder straps 376 in this and other embodiments may have portion formed of a material to which hook portions of hook and loop fasteners may be attached for wear with the cape or other supplemental supports. Similarly, each of the embodiments shown in FIGS. 24a-25b have loop portions at the front ends of the shoulder straps and the side straps as well as across the top center of the back. The waist band at the back may have an internal elastic band with a silicon grip coating to prevent riding up at the hip.

Figure 24A:
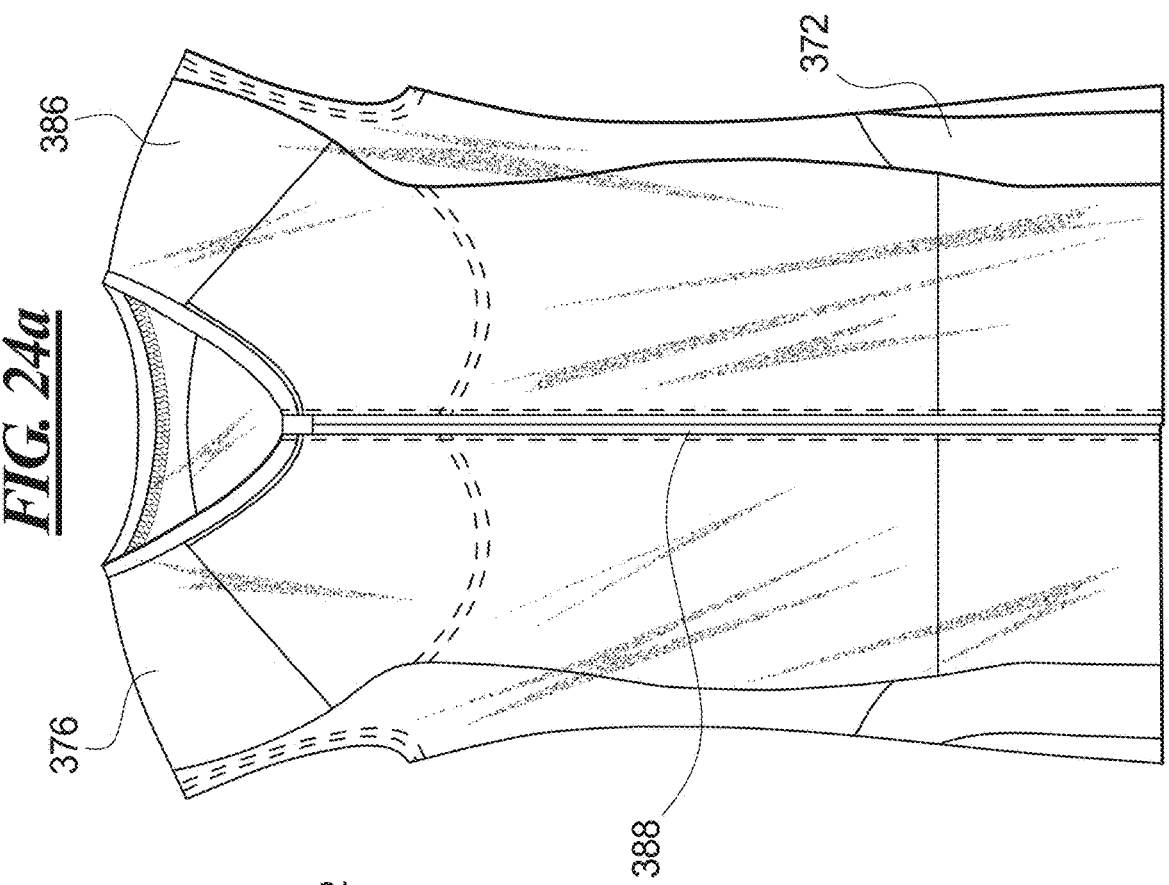
FIGS. 24a and 24b are front and back views, respectively, of a woman's sleeveless zipper front garment of yet a further embodiment, selected straps being shown in exploded view.
Figure 24B:
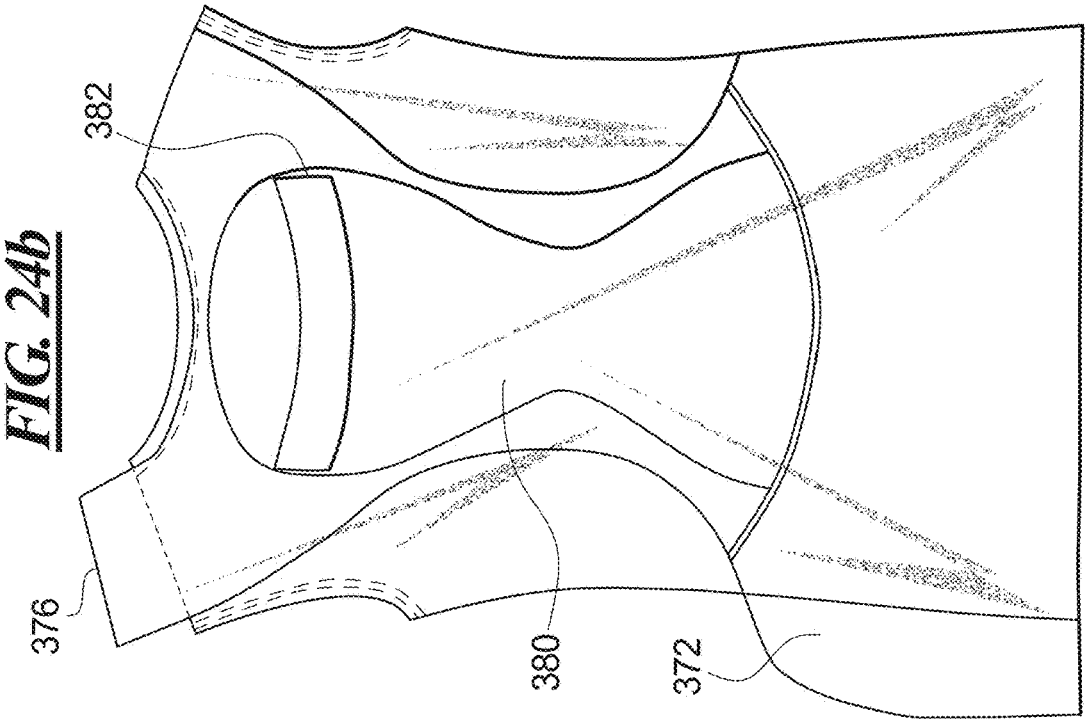

In FIGS. 24a and 24b is provided a front zipper sleeveless woman's shirt 386 that includes a front closure 388, such as a zipper or other closure, but is otherwise identical to the sleeveless shirt of FIGS. 23a and 23b. The details will not be repeated for the sake of brevity.

Figure 25A:
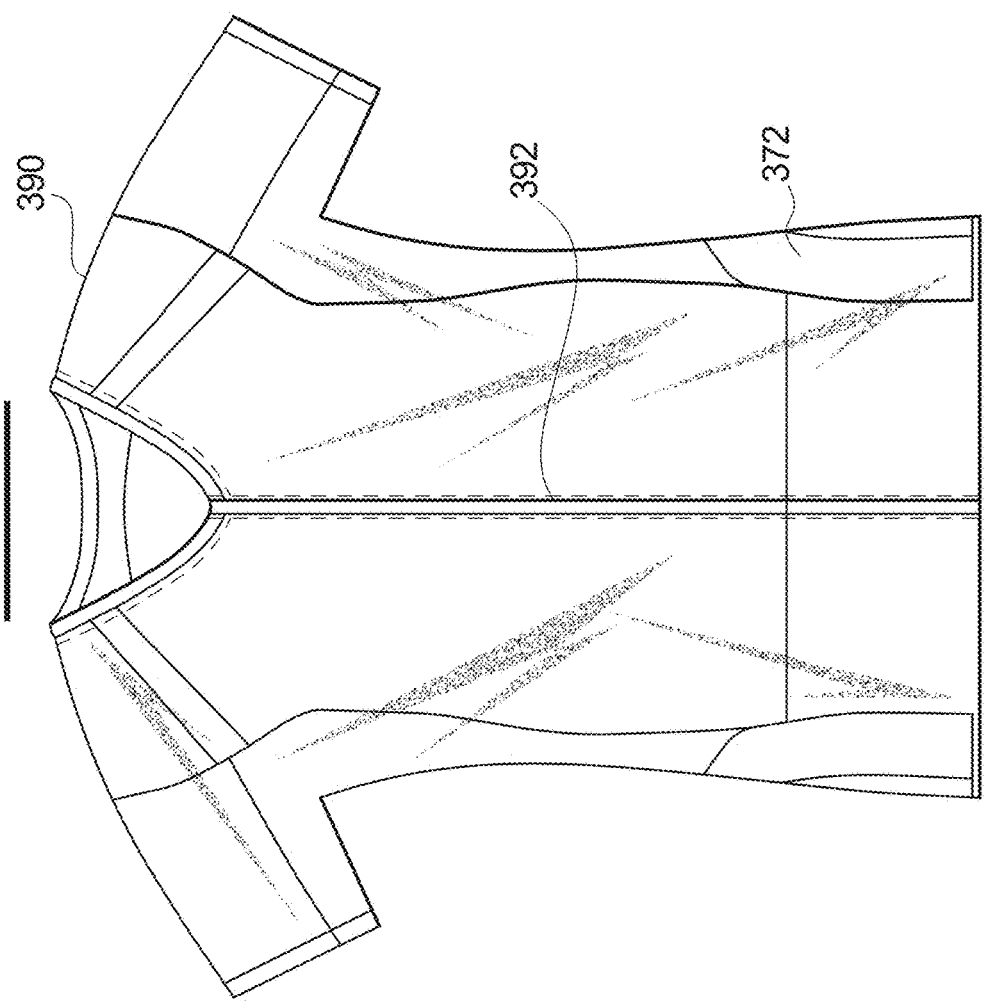
FIGS. 25a and 25b are front and back views, respectively, of a man's or child's short sleeve zipper front garment of still another embodiment, selected straps being shown in exploded view.
Figure 25B:
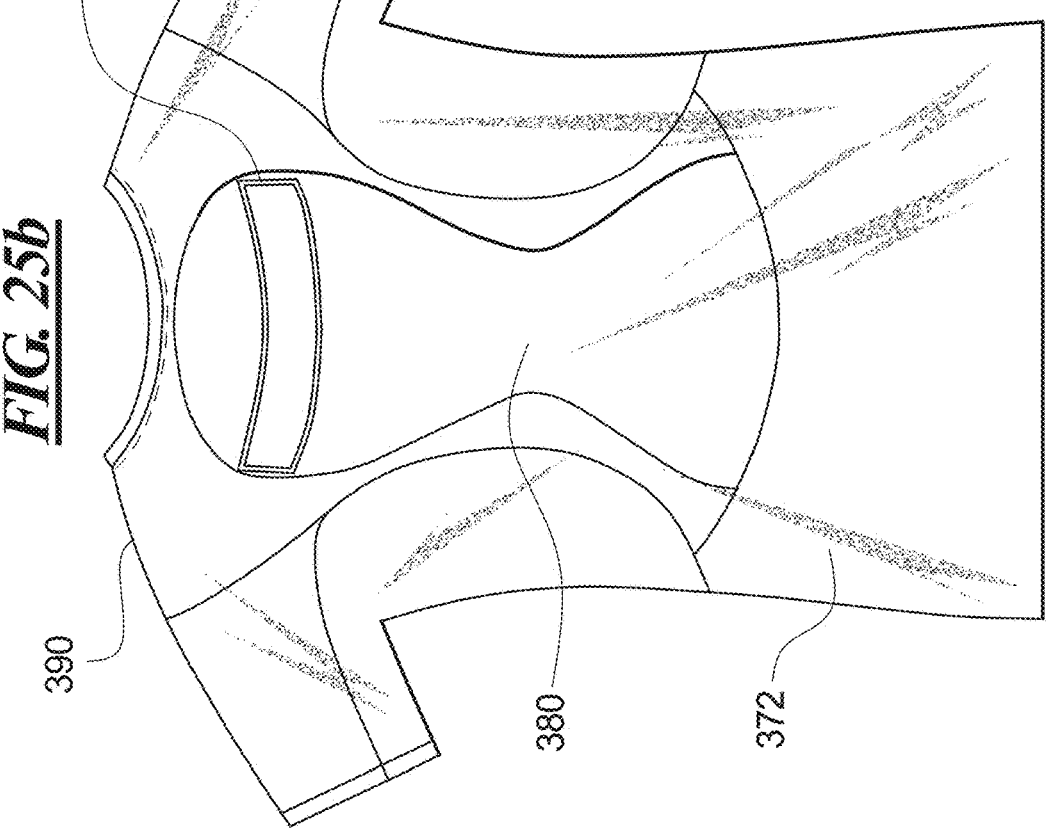

A short sleeved shirt 390 that is unisex and may be sized either for adults or children is shown in FIGS. 25a and 25b. The shirt 390 has a front closure 392 such as a zipper or other closure. The shirt 390 includes features of other garments described herein and so will not be described in further detail.

Figure 26B:
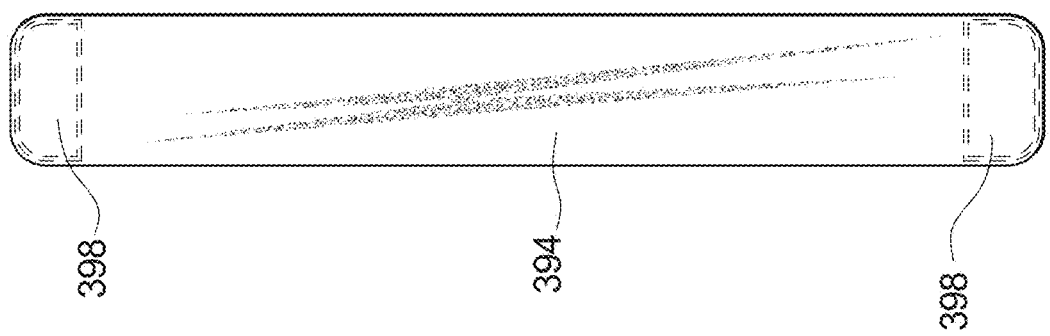
FIGS. 26a and 26b are front and back views of auxiliary straps for use with embodiments of the present garments.
Figure 26A:
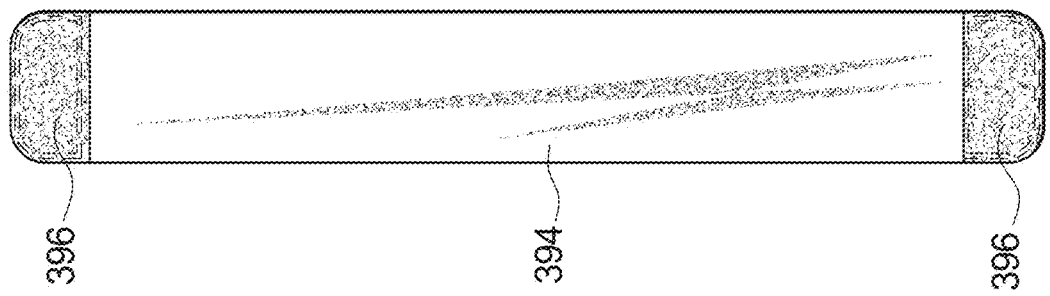

FIGS. 26a and 26b are front and back views of a supplemental strap 394 that is formed of an elastic material in certain embodiments and in other embodiments is formed of a fabric with a predetermined elastic characteristic. The strap 394 has fasteners 396 at each end. The fasteners 396 of certain embodiments include hook portions of hook and loop fasteners. The fasteners 396 enable the wearer to affix the strap 394 to garments, such as those shown herein or others to provide supplemental support to the wearer. The straps 394 may be applied and worn individually or may be used together with plural straps or other supplemental supports, as needed. The strap 394 may have grips 398, such as rubberized grips, at the end on the opposite face from the fasteners 396, or the bands may be provided without the grips. Similar grips may be provided on straps as are provided in accordance with the present specification. The supplemental strap 394 or neuroband may be provided in a variety of lengths as needed. For example, a four inch long version may be provided for attachment to the loop portion strip at the upper back of the garment. Bands of lengths of 18 inches to 32 inches in two inch increments may be provided in certain embodiments.

Figure 27B:
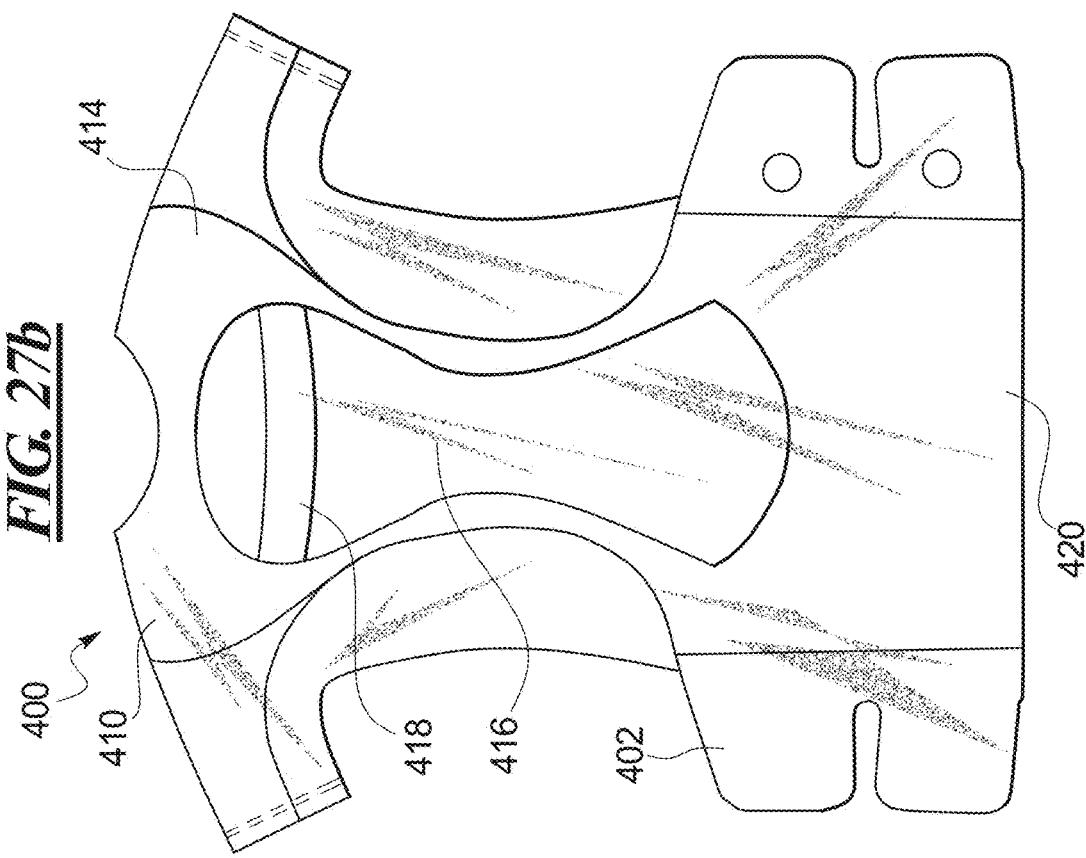
FIGS. 27a and 27b are front and back views, respectively, of a man's or child's short sleeve zipper front garment of an embodiment for prescription wear, for example.
Figure 27A:
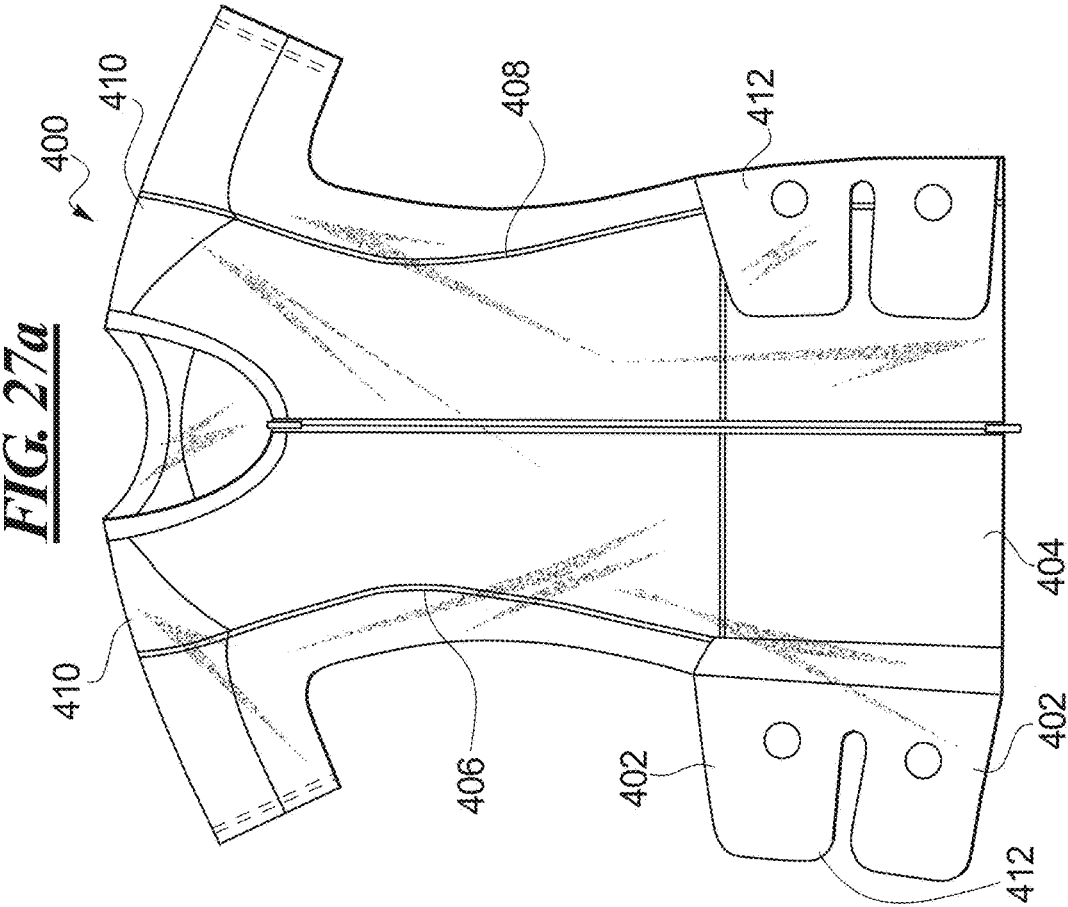

In FIGS. 27a and 27b is shown a zipper front shirt 400, such as for wear by men or children, that provides further support such as may be prescribed by a doctor or other healthcare professional, although a prescription may not be required to obtain or wear the garment. Adjustable side straps 402 extend from the sides of the lower portion of the shirt 400 and are fastenable to a lower portion 404 of a front panel 406. The front panel includes a closure 408, such as a zipper. The front panel 406 is attached at its top end to shoulder straps 410. Circular features 412 are provided on the side straps 402 to indicate thumb holes or finder holes so that additional tension may be applied to the straps. The holes 412 may be provided closer to the ends of the straps.

In the back view of FIG. 27b the shoulder straps 410 connect to or are part of the strap panel 414, on which is the core portion 416. The core portion has the arcuate strap 418. The lower back portion 420 provides support for the lower portion of the body core. By applying tension to the side straps 402 and affixing them to the lower portion 404 of the front panel 406, the wearer provides activation and support for muscles of the wearer through tension and elasticity, bringing the tension back to the body core of the wearer and promoting body posture and movement. A similar configuration may be provided for women.

Figure 28:
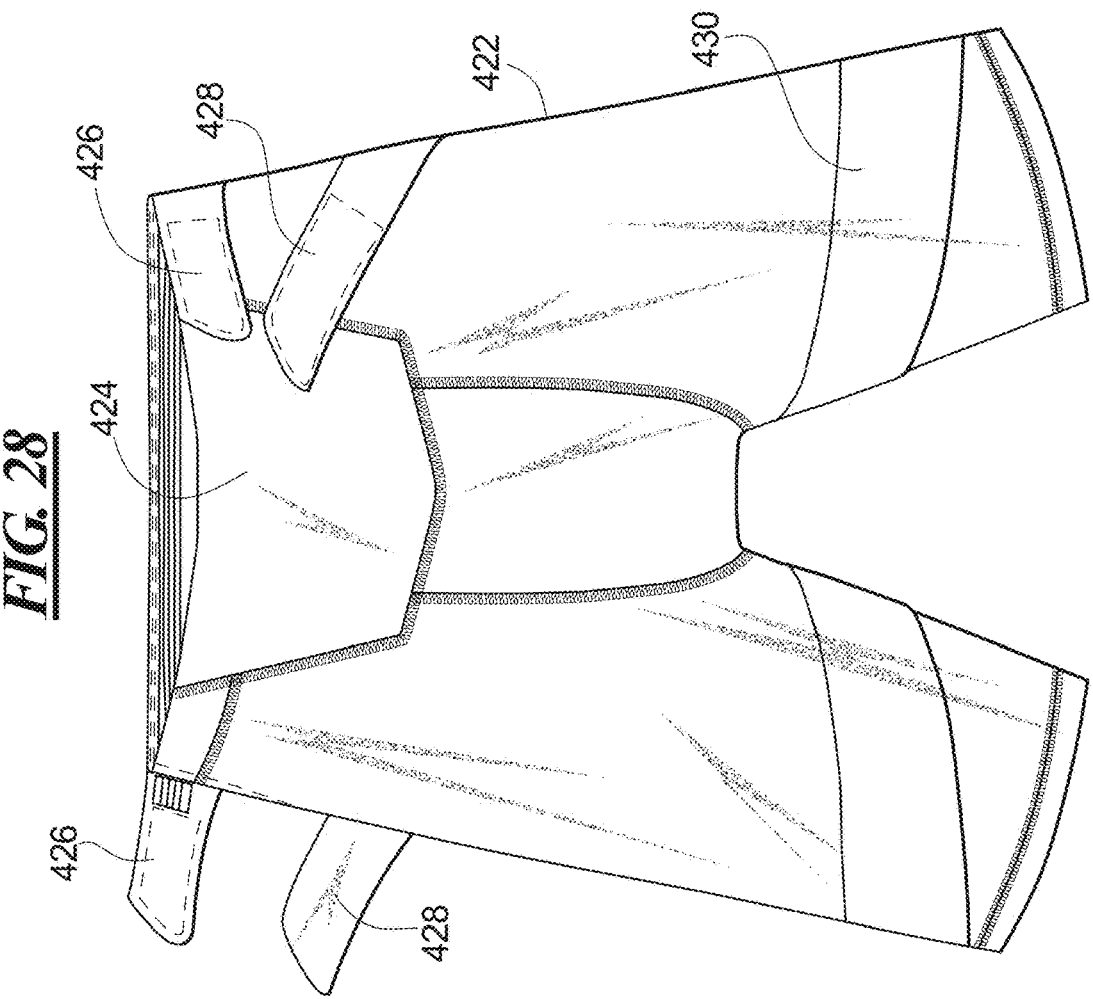
FIG. 28 is a front view of another embodiment of a shorts garment.

FIGS. 28, 29a, 29b and 29c illustrate other versions of shorts, the shorts may be referred to as a core chassis. The shorts 422 of FIG. 28 include a front panel 424 to which may be attached the waist straps 426 and the hip straps 428, such as by hook and loop fastener. The hip straps 428 may wrap around the leg at 430 or the strap 430 may be separate from the hip straps 428. The straps are neurobands to stimulate and support muscles and muscle groups. The shorts of FIGS. 28 and 29 are side opening shorts.**

Figure 29A:
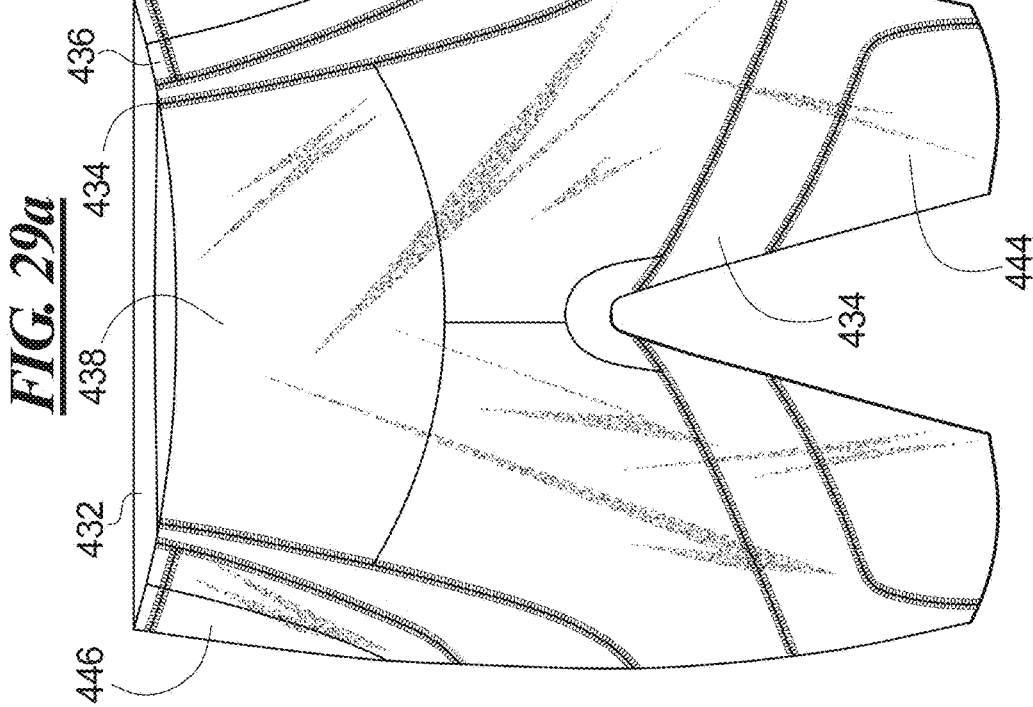
FIGS. 29a, 29b and 29c are front, back and side views of a further embodiment of another embodiment of shorts.
Figure 29C:
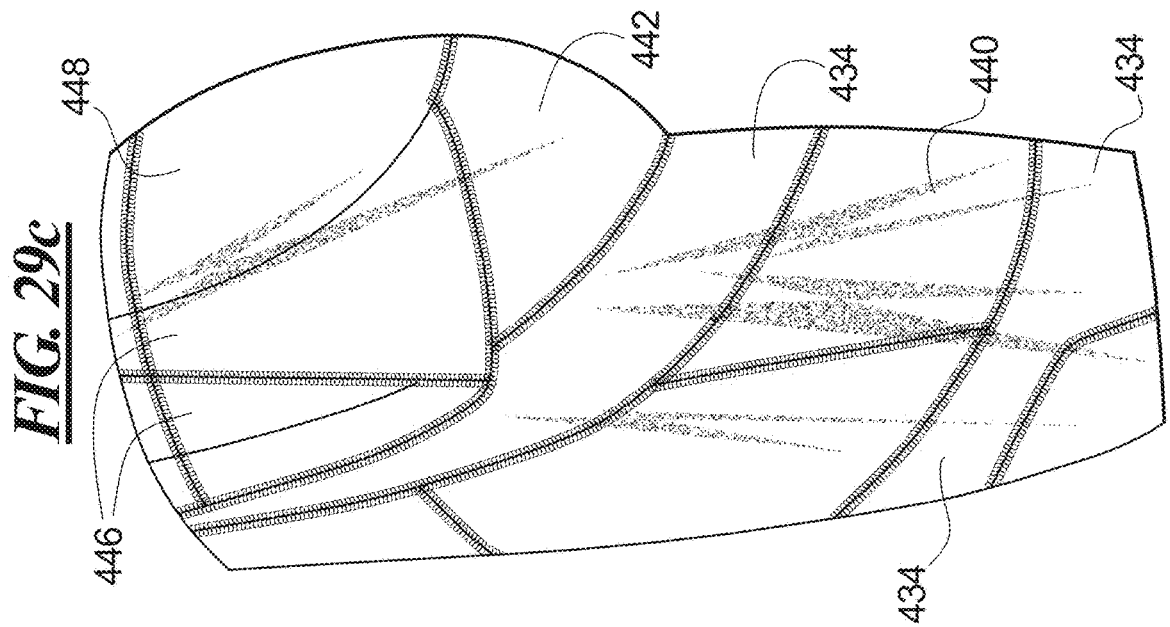
Figure 29B:
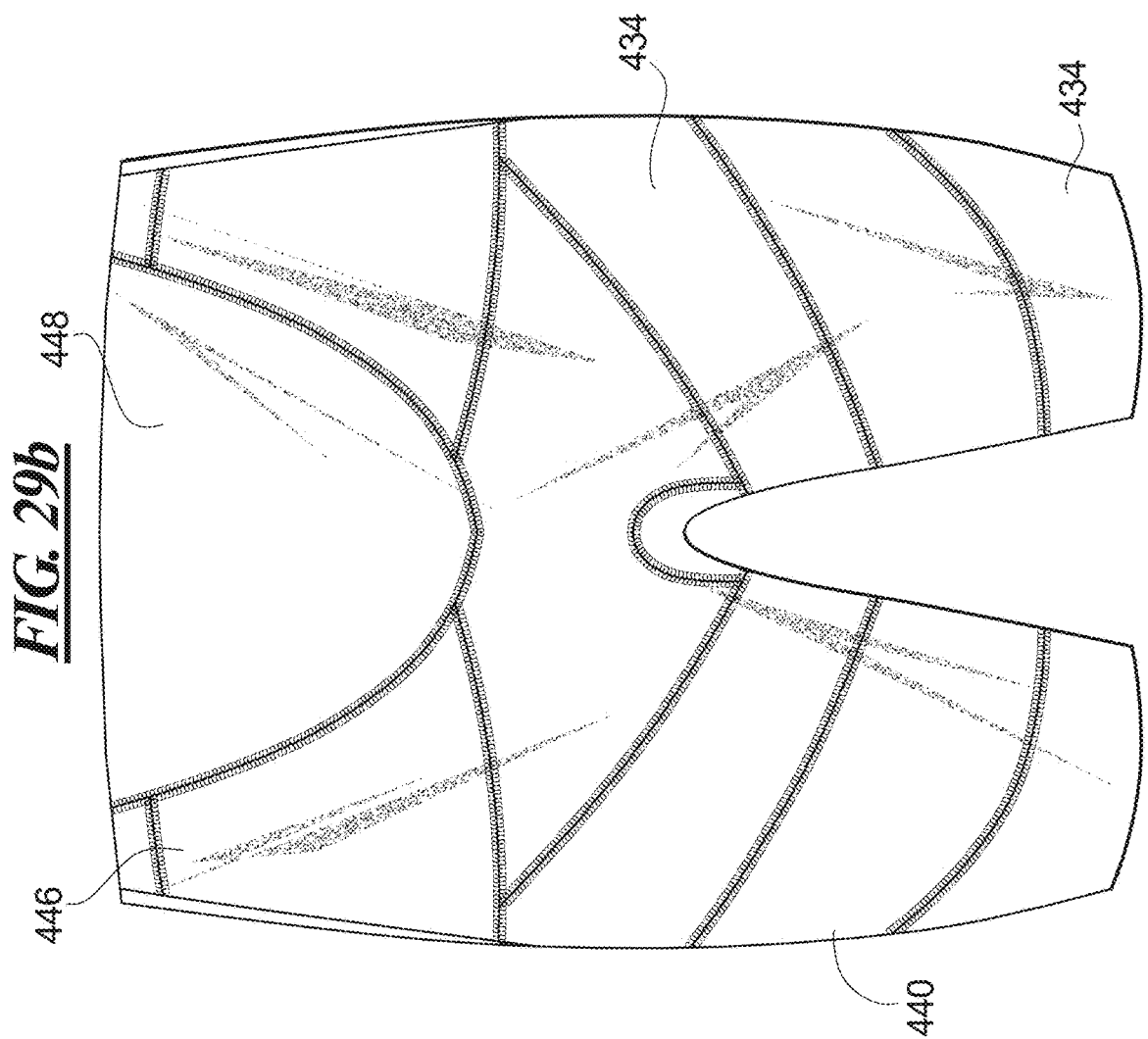

The shorts 432 of FIGS. 29a, 29b and 29c include straps 434 that extend from the waistband 436 on either side of a front panel 438 and are generally vertical at an upper front of the shorts. The straps 434 curve around the back of the leg 440 below a seat 442, then spiral around to the front of the leg 440 and connect to the lower hem 444 at the outsides of the legs 440. The lower ends of the strap 434 extend about the lower hem 444 at the back of the legs 440. Spiral tension is applied to the wearer's lower extremities by the straps 434.

The shorts 432 may include side fasting panels 446 that permit the wearer to don the garment and then secure the garment in place using the side fastening panels. A lower back panel 448 is provided at the waistband 436 at the back of the shorts 432.

Turning to FIGS. 30a and 30b, an alternative embodiment of a crop top or bra top 450 is provided. The top 450 includes a front panel 452 that is connected to two shoulder straps 454 and 456. The inner shoulder strap 454 extends to a seam 458 where it is stitched to the front panel 452 in a seam that extends generally perpendicular to a seam 460 that connects the outer shoulder strap 456 to the front panel 452. The extended seam interface between the front panel 452 and the two shoulder straps 454 and 456 provides a greater degree of support to the front panel 452. The front panel 452 and the shoulder straps 454 and 456 are of fabric that has a low stretch characteristic, such as French terry.

Between the shoulder straps 454 and 456 is a mesh panel 462. Side panels 464 are provided connected to the front panel 452. A distinction between the embodiment of FIGS. 30a and 30b and the embodiment of FIGS. 18a and 18b is that the top of FIGS. 18a and 18b include two mesh panels between the shoulder straps and the neckline whereas the embodiment of FIGS. 30a and 30b includes a single mesh panel between the shoulder straps and the neckline. The embodiment of FIGS. 30a and 30b has a more open neckline, particularly at the back.

With reference to the back of the top 450 as shown in FIG. 30b, the shoulder straps 454 and 456 connect to a center strap 464. The center strap has a wider portion between the lower, outer shoulder straps 456 and tapers to a narrower width toward the neck 466 and the lower hem 468. The inside of the lower hem may be provided with a grippy material, such as a silicone material, part way or all the way around. Similar grippy material coatings or layers may be provided on other embodiment as disclosed herein.

Two mesh panels 470 are provided on either side of the central strap 464. Two portions 476 are between the shoulder strap 456 and the side panels 464. Two diamond shaped patches 472 are provided on the lower, outer shoulder straps 456. The patches 472, which may be of any shape, including of a bar or strip shape, are formed of a loop portion of a hook and loop fastener. An elastic band 474 is connected to the patches 472 by hook portions of a hook and loop fastener. The elastic band 474 provides tension horizontally across the middle of the back which may benefit some wearers. The elastic band 474 of certain embodiments is approximately four inches in length and has the hook fasteners stitched to the inside surface adjacent the ends. The elastic band 474 provides tension to the scapula, and may be referred to as a scap tab. The elastic band 474 or a similar short band may be provided on any of the shirts or tops that have a fastener at a location for fastening such a band. For instance, several of the tops and shirts described herein include bands or strips of loop material on the back and may have an elastic band attached thereto as desired by the wearer. Of course, the attachment locations and bands may be of any location, configuration or of any fastener.

Examples of materials used in the embodiments shown herein include: jersey fabric of 85% poly and 15% spandex for the front body, a mesh fabric of 75% nylon and 25% spandex for the mesh panels, and 100% poly French terry fabric for the neurobands. Seams are stitched with four thread overlock stitching using tiger 35 thread for overlock stitching and flatlock stitching is stitched with tiger 35 thread and a flatlock top spreader, a flatlock bottom looper, or using a flatlock needle. Double stitching is provided using a ⅛ inch double needle cover stitch, a double needle coverstitch needle, or a coverstitch bottom looper.

For other embodiments such as the embodiment of FIG. 4, a front panel of single jersey stretch cots of 94% cotton, 6% lycra, a center back panel of baby French enzyme compactor of 100% cotton, an overlay center back panel and lower side front panels of japan Velcro plush fabric plus neoprene, and side and shoulders of interlock stretch CVCS Xco 54% cotton and 36% PES+Sp10. Threads used are to be stretchable for use with a high stretch fabric and are provided in a four needle flatlock stitch, a two needle coverstitch and a single needle cover stitch.

For the short embodiments, an example includes front and back and legs of single jersey fabric of 60% polyamide and 40% elastane, bonded leg panels of fabric of 77% polyamide and 23% elastane with a YSO coating on the back side, the back waistband panel is bonded to the inner back side and is of tricot with 500% polyamide and 50% elastane, and the folded front waistband panel is of stretch Velcro fabric of 78% nylon and 22% spandex. Antigripper elastic is provided on the inside of the back waistband.

The embodiments relate to a posture control system that uses the modality of controlled and selective resistance to provide dynamic posture control and/or posture therapy throughout the body. In many ways the posture control system can be thought of as an orthosis; the term orthosis being defined by medical science and the FDA as 'an orthopedic appliance or apparatus used to support, align, prevent, or correct deformities or to improve function of movable parts of the body.' Unlike a traditional orthosis the posture control system uses a wearable chassis that form fits to the user's body, such as a garment or elastomeric chassis. Additionally, the chassis incorporates anatomic anchor points to mount selective resistance that enables rigid and/or semi-rigid tensions to be coupled from muscle to muscle, joint to joint and from lower to upper extremity. The coupling schemes allow controlled external tension to be placed onto the posture chassis to assist in the transfer of musculoskeletal forces in line with the direction of motor control and the science of kinesiology. The posture control system may comprise a chassis that is based on one or more garments worn by a user. The garments may be configured as a controlled resistance system to provide coverage over the wearer in whole or in part as desired. The garment/posture control system may comprise, for example, an upper chassis (such as a shirt) that is coupled to a lower chassis (such as a pair of pants or shorts). The garments may use various combinations of tactility and elasticity to help the wearer's posture, for example, with various panels, stitching, etc. As part of the posture control system, the garments may also comprise or be configured with various attachment points that also perform as anatomic anchor points to provide the user with controlled tension or resistance segments to align the wearer's posture as desired. Other types of garments may be included in the posture control system, such as socks, jackets, hats, gloves, etc. In addition, the posture control system may accommodate other types of wearable items, such as helmets, braces, etc. These items may be coupled to the chassis or other portion of the posture control system using various known attachments, such as straps, cabling, etc., that are rigid or non-rigid.

In poor body alignment, it is determined that a kinesthetic, proprioceptive, or balance deficit exists. This poor body alignment can then cascade into a variety of conditions and/or pain. In some embodiments, the posture control system comprises various components that are configured to emphasize kinesthetic exercise and low-level functional exercises and fundamental neuromuscular coordination. The selective resistance can facilitate virtually any closed or open kinetic chain training exercise by increasing the amount of kinesthetic and proprioceptive balance feedback to the body for better postural control. Examples of exercises that selective resistance can facilitate include biofeedback training in open and closed kinetic chain positions, co-contraction exercises, balance exercises, low-level functional exercises, and fundamental neuromuscular coordination drills. In some embodiments, these functional components may be attached to or integrated with one or more of the garments in the chassis of the posture control system. In addition, the posture control system may comprise garments that are coupled together, for example, with straps, and/or, a cape-like accessory, in unique fashions that align body structures for kinetic biofeedback.

In some embodiments, the posture control system comprises various components that are configured or comprise features to stimulate nerves to actively influence sensory and motor pathways to assist with posture. In some embodiments, these components may be attached to or integrated with one or more of the garments in the chassis of the posture control system. According to one aspect, the embodiments provide force, resistance, or parasitic energy for purposes of posture control and/or therapy. In one embodiment of the posture control system, the various garments use levers and anatomic anchor points to which can be attached various tension or resistance segments that provide kinetic biofeedback. In addition, the posture control system may comprise garments that are coupled together, for example, with straps, and/or, a cape-like accessory, in unique fashions that align body structures for better posture.

The posture control system may also accommodate other features. For example, the posture control system may comprise various pouches or compartments to allow for the delivery of drugs or medications as well as various forms of stimuli, such as electro-stimuli, cold therapy, heat therapy, accelerometers, gyrometers, etc. The pouches or compartments may also comprise rigid materials or structures that are capable of providing musculoskeletal support.

The embodiments may used to treat various ailments or conditions. In addition, the embodiments may be used in treatments of other types of conditions in which good posture provides benefits. For example, the posture control system may be employed to treat injuries, pain, musculoskeletal conditions, and neurologic conditions, such as autism, cerebral palsy, etc. In some embodiments, the posture control system may be configured as an orthosis device. As an orthosis device, the posture control system or portions of the system provides a selective resistance orthosis intended for medical purposes that is worn on the upper or lower extremities, or traverses and couples the upper and lower extremities to support, to correct, or to prevent deformities or to align body structures for functional improvement.

Certain embodiments of the inventions will now be described. These embodiments are presented by way of example only, and are not intended to limit the scope of the inventions. Indeed, the novel methods and systems described herein may be embodied in a variety of other forms. Furthermore, various omissions, substitutions and changes in the form of the methods and systems described herein may be made without departing from the spirit of the inventions. To illustrate some of the embodiments, reference will now be made to the figures.

The features and attributes of the specific embodiments disclosed above may be combined in different ways to form additional embodiments, all of which fall within the scope of the present disclosure. Although the present disclosure provides certain embodiments and applications, other embodiments that are apparent to those of ordinary skill in the art, including embodiments, which do not provide all of the features and advantages set forth herein, are also within the scope of this disclosure. Accordingly, the scope of the present disclosure is intended to be defined only by reference to the appended claims.

The human body moves in an alignment inherent in a species that evolved to balance and walk upright on two legs. How the human form aligns itself to move optimally is ever-dynamic and occurs in a kinetic chain from the appendages to the body's core. As will be explained further below, the posture control system may serve as a posture aid or therapy to help the wearer achieve and maintain a healthy alignment and posture of their body.

Some embodiments are designed to provide a systematic application of comfortable, form-fitting posture garments constructed with anatomic anchoring points that accept materials with specific tensile strength and tactile feel to create a novel means to synchronize biomechanical support, neuromuscular stimulation, and sensory feedback. In one embodiment, a controlled resistance system is configured to facilitate the body's own physiological process of posture control, (for example, based on parasitic support), optimal mobility, and the confidence and physical attractiveness linked to good posture and form.

Approaches to health are best performed when facilitating the body's own biological powers for recovery. The embodiments provide tensile support, selective resistance (e.g., orthosis), for example, based on musculoskeletal need, and tactile intervention mounted into comfortable, form-fitting garments to facilitate the functions inherent in the nervous and musculoskeletal systems.

Nerves stimulate muscles (creates force) when the muscle is stimulated it may contract or lengthen. Muscular movement occurs when the nerve stimulates the muscle to perform a specific act.

In the embodiments, the musculoskeletal system is viewed as a linkage system. When one part moves another part must also move to accommodate that movement. Muscles attached to bone move the bone that in turn move the body. Some embodiments are based on multiple scientific and professional medical disciplines who are aware of the type and placement of stimuli needed to achieve a desired change in biomechanics and biofeedback forces for the betterment of musculoskeletal alignment and good posture maintenance throughout the body. Accordingly, some embodiments provide a neuromuscular enhancement system for posture correction and maintenance.

In general, the embodiments may provide some of the following functions:
POSTURE CORRECTION AND POSTURE MAINTENANCE
BIOMECHANICAL SUPPORT
NEUROMUSCULAR BIOFEEDBACK
KINETIC BIOFEEDBACK
KINETIC ALIGNMENT
CONFIDENCE AND PHYSICAL ATTRACTIVENESS Posture is often misunderstood being thought of in terms of a static position like standing or sitting. However, the embodiments appreciate that human posture is dynamic, i.e., posture is also the body in motion. The anatomy and physiology that supports posture is dynamic as well and always in a constant state of motion and balance.

For example, posture is defined in the Journal of America Medical Association (JAMA) as the "sum total of the positions and movements of the body throughout the day and throughout life." Posture has a direct relation to the comfort, mechanical efficiency and physiologic functioning of the individual. Poor posture is also a main risk factor in many injuries. For example, poor posture can impede the ability of the lungs to expand. Posture, when correct, helps to increases one's ability to breathe and allows muscles to work at optimum capacity. When slumped over, the lungs have less room to contract and inflate, therefore, decreasing its capacity to obtain the maximum amount of oxygen needed.

An individual's posture is the foundation for mobility performance regardless of age or demographic. As noted, poor posture leads to spinal pain, headaches, mood problems, chronic fatigue, increased chance of injury and decreased lung capacity among other problems. Furthermore, modern technological society has created a platform for poor postural behavior.

The embodiments recognize that posture is supported by the musculoskeletal system and regulated by the nervous system. The two combined physiologic functions produce neuromuscular control.

For example, the embodiments recognize that postural control is dependent upon the conscious and unconscious reception and acceptance of external sensory stimuli by the individual and the individual is responsive to external stimuli in the waking and the sleeping state.

In some embodiments, a garment system using selective resistance is configured as an external means that is in contact with the wearer's skin to actively influence the external stimuli received by the individual to effect neuromuscular control for the betterment of posture. The embodiments are configured to facilitate the biomechanics of body movement, which occurs in a kinetic alignment to and from the body's core. Tissue is used to support it.

In addition, some embodiments assist or employ the tensile strength of collagenous muscle tissue and that it has various properties related to its ability to produce force and movement about joints, such as irritability, contractility, extensibility, and elasticity.

In some embodiments, the posture control system comprises a garment system using selective resistance that uses the tensile properties of elastomeric materials to contract and develop tension or external force against resistance when stretched. The embodiments may use materials with tactile properties to stimulate the 'irritability' property of muscle tissue for the purpose of providing external biofeedback. In addition, posture control system may be designed to provide heating and or electrotherapy, cooling, rigid or semi-rigid panels, accelerometers, radio frequency, lumbopelvic supports, etc., depending on the desired form of posture control or therapy, and pain management.

The garment system may also comprise other various features, such as pockets, pouches, and other forms of accessories. The garment system may also comprise enhancements such as a drug delivery system, electrostimulation systems, heating and cooling, etc.

It is recognized that balance and motor control is built upon a living network of biofeedback to and from the central and peripheral nervous systems that constantly adapts to an individual's external and internal environment. The reflex mechanisms by which we maintain balance and equilibrium within our environment are learned and rely heavily on muscle memory patterns. Kinetic biofeedback is a means of gaining greater awareness of these physiological functions and the embodiments use techniques that can manipulate them. That is, feedback that is in line with the kinetic motion of muscles.

For example, some embodiments use tensile support and tactile intervention, such as providing light to moderate resistance and support in line with muscle biomechanics, as a novel means to influence kinetic biofeedback.

The embodiments may be configured to influence the conscious and mostly subconscious processes of balance and equilibrium by inducing biofeedback with predictable external touch and tension patterns of anatomically placed banding, strapping or cabling. The posture control system may be designed to be worn for various periods of time to provide a desired effect. For example, the changes to a wearer's posture may be maintained with periodic or ad-hoc use by a user. Some embodiments influence the conscious and mostly subconscious processes of balance and equilibrium by inducing biofeedback with predictable external touch and tension patterns of anatomically placed banding, strapping or cabling.

In one embodiment, a posture garment is constructed with elastomeric materials having distinct properties of elasticity, tensile strength and tactile intervention. The garment may be constructed using seams that have specific stretch characteristics that are directionally placed in line with the elastomeric materials they enjoin. Seam placement and elasticity may be based on the science of human kinetics and placed in such a way to create the least obstructive means to facilitate the transfer of external loads placed onto the garment.

In one embodiment, as noted above, the garment system/posture control system serves as a chassis that is constructed with anatomic anchor points. The mounts provide modularity by providing support to muscle tissue that is adaptable to the users needs.

In various embodiments, the garment system may be designed for the upper and lower extremity or portions of a human user, such as in the form of shirts, pants, shorts, etc., alone or in combination. In addition, the garment system/posture control system may comprise various coupling mechanisms to traverse the upper and lower portions of the garment system/posture control system and couple them together as functional unit that helps posture.

The posture control system is configured to surround the anatomy in a comfortable form fit designed to stabilize or to fixate various anatomic areas to enable anchor/lever points and to allow segments of tension or resistance segments, such as Neurobands, to exert force and move in a specific direction.

Tension or Resistance Segments (e.g., Neurobands) and Posture Control System as 'Kinetic energy harvesting".

Energy harvesting (also known as power harvesting or energy scavenging) is the process by which energy is derived from external sources. In some embodiments, the posture control system employs a wearable power harvesting technology using principles of motion to unobtrusively generate neuromuscular activity from the natural motion of walking and then use it to control posture. That is, the energy source for the posture control system kinetic is harvested from the friction between the tension or resistance segments onto muscles and joints. For example, controlled resistance provided by the posture control system or garment converts mechanical strain into different sources of energy such as thermogenesis (muscle heat) and increased metabolism produced from wearing the posture control/garment system upon muscle tissue. In this manner biomechanical energy is being harvested to reduce fatigue by facilitating better posture control.

The garment chassis forms a firm base for the anatomic mounts, such as Posture Mounts, and tension or resistance segments, such as Neurobands, across various muscle groups and joints. The garment system can thus be synergistic with the tension segments and allowing them to carry out their specific movements relative to the specific resistance and tactile intervention they provide. In some embodiments, the posture control system is designed to distribute forces to and from the center of gravity also known as the human center of rotation.

In some embodiments, the garment system can be configured to be prime movers for the action to provide neuromuscular support and stimulation. Accordingly, the specialized resistance of the garment system can refine movement and rule out undesired motions.

Muscle Tissue Properties and Design Features to Enhance them

As noted, the posture control system is configured to influence muscle tissue behavior and contraction. Below are some of the muscle tissue properties that have been found to be useful and some examples of design features that may be implemented in the posture control system.

Irritability is a property of muscle being sensitive or responsive to chemical, electrical, or mechanical stimuli. In some embodiments, the tension or resistance segments provide mechanical stimuli and comprise materials used to provide tactile intervention with muscle.

Contractility is the ability of muscle to contract and develop tension or internal force against resistance when stimulated. In some embodiments, the tension or resistance segments comprise tensile properties of materials used to support muscle.

Extensibility is the ability of muscle to be stretched back to its original length following contraction. In some embodiments, the tension or resistance segments provide elastomeric stretch characteristic of materials used to support muscle contractions.

Elasticity is the ability of muscle to return to its original length following stretching. In some embodiments, the tension or resistance segments provide elastomeric stretch characteristic of materials used to support muscle contractions. Human movement is always dynamic and the axis of materials, such as neuroband placement, is configured not to compress muscles, but to support muscle contractions. In one embodiment, the axis of materials is configured to support the axis of rotation of the core.

Core stability may been defined as the lumbo-pelvic hip muscle strength and endurance yielding a coordinated activation of muscles and maintenance of alignment throughout the kinetic chain. The embodiments may be configured to enhance or employ core stability and incorporate it into the posture control and therapy.

Exemplary Garment System

In one embodiment, the garment system/posture control system is a modular system having components that anatomically and physiologically organize with one another.

The average adult male is about 60% water. The average adult woman is about 55% water. 90-95% of the remaining weight is comprised of over 600 skeletal muscles.

There are 215 pairs of skeletal muscles, which usually work in cooperation with each other to perform opposite actions to balance and align the joints, which they cross.

Aggregate muscle action refers to when the muscles work in groups rather than independently to achieve a given joint motion. In general, muscles have contractual properties, they don't compress and will respond adversely to prolonged compression.

Types of Muscle Contraction

Concentric—Shortening or Toward the Middle of the Belly of the Muscle.
  muscle develops tension as it shortens
  occurs when muscle develops enough force to overcome applied resistance
  causes movement against gravity or resistance
  described as being a positive contraction Eccentric—Lengthening or Away from the Middle of the Belly of the Muscle
  muscle lengthens under tension
  occurs when muscle gradually lessens in tension to control the descent of resistance
  weight or resistance overcomes muscle contraction but not to the point that muscle cannot control descending movement Isometric or Static Contraction without Change of Length
  the speed (or velocity) of movement is constant
  muscular contraction (ideally maximum contraction) occurs throughout movement Isotonic muscular tension remains constant while the muscle either shortens or lengthens. Isotonic—equal tension Isokinetic means equal or the same this means that the Isometric or static contraction without change of length
  the speed (or velocity) of movement is constant
  muscular contraction (ideally maximum contraction) occurs throughout movement The tension or resistance segments, such as Neurobands, may behave like muscle groups and can contract to control motion in multiple directions and/or planes.

The senses are the physiological means by which organisms provide data for how we perceive our environment. Their operation, classification and theory are exhaustive leading to difficulties in defining how and what the senses perform and in particular, how the multitude of senses interact with one another. The embodiments can provide a garment construction that affects the input to the senses of balance (touch, equilibrioception, proprioception) and sense of motion/acceleration (kinesthesia). These senses work together to keep a wearer balanced when sitting, standing, walking or running.

The senses of touch, proprioception, kinesthesia and equilibrioception are related in subtle ways, and impairment in any one of them can cause large deficits in perception and action. Some embodiments can provide a touch-tension interface with built in touch or resistance segments, such as Neuroband™ panels, mounted in a comfortable, form-fitting garment.

Of note, the stretch panels and garment construction is not necessarily designed to be compressive or to resemble a compression garment. Rather, these features of the garment apply external stretch characteristics that can enhance the senses of balance and motion, all which can be of importance.

The exemplary interactive garments with customized touch and tension mechanisms can influence the user's external environment and why it may improve a wearer's posture, motor control, etc. By wearing the posture control system of the embodiments, it is believed the unconscious application of an external touch-tension feedback system can facilitate or modify the muscle firing in the wearer's sensory and motor pathways and result in various therapeutic effects.

The bioengineering requirements of a therapeutic garment device to help stimulate neuromuscular balance have not been solved by the known technology or products. In contrast, some of the embodiments have addressed the failings of the prior art by including garments that provide an amount of tension or torque to transfer body forces to and from the user's core. The garments have adaptability and comfortable functionality and can be distinguished from conventional known compression garments which have little or no basis in science and provide little data that they produce a positive cause and effect.

The exemplary posture garments may work for all peoples and populations equally, simply because all bodies have an innate need for balance and desire good posture. The way the exemplary posture garments perform can be viewed as having similar effect as eyeglasses worn because eyes don't bend and focus well given pathology in the performance of our optic anatomy. To see better, specifically shaped lenses are worn as an external device to help pull and bend optic anatomy in ways the individual cannot. Similarly, the exemplary posture garments and garment system applies posture control and therapy to the anatomy to support muscles and joints while delivering kinetic biofeedback to influence good posture in ways the body not.

The specific touch and tension of the exemplary tension or resistance segments, such as Neurobands, leverage the initial external stimulation with muscular support and interactive kinetic biofeedback. This may be referred to as actionable-biofeedback. The garment construction is non-restrictive, comfortable and enhancing to joint range of motion.

The embodiments are based on proprioception and kinesthesia to enhance and preserve good posture. Proprioception is the sense of where the body is in time and space. A loss of the sense of proprioception over time may cause the muscle to lose balance. Like so many of the senses, the sense of balance and movement eventually become a largely unconscious process—Reflex actions occur in milliseconds, which is beyond the brain's cognitive comprehension. In simpler terms, a person can normally balance, move and rarely does the person have to consciously think about it. In some embodiments, the garment system/posture control system provides dynamic actionable-biofeedback to influence the user's sense of proprioception.

Muscle Mirroring

Good posture puts a body in a form that will expend the least amount of energy required to move. Good posture connects optimal body kinematics. The embodiments influence kinematics by placing the stretch characteristics of the garment system or posture control system line with the transfer of muscle force from the body limbs to the body's core or center of gravity. This directional placement may be referred to as muscle mirroring or kinetic muscle mirroring. Muscle mirroring provided by the posture garments of the embodiments differ from compression garments because the garments don't compress muscle tissue; they stretch with it, i.e., the garment substantially mirrors the muscles of the wearer especially when in motion. In this manner, the exemplary embodiments provide actionable biofeedback by mirroring muscle contractions that cannot be provided by conventional garments, such as compression garments.

Like cognitive intelligence, muscle intelligence is quite refined. Muscles have memory and muscle memory involves the ability to reason, plan, solve movement problems, comprehend complex movements, learn quickly and learn from experience. Muscle intelligence involves patterns of muscle activity called reflexes that allow rapid and coordinated movement responses. Reflexes respond to changes in environmental stimuli that at times do not involve the brain's centralized control. The speed and amount of energy required for a reflex response to occur is a primary factor in reducing physical fatigue, injury and the inflammatory cycle.

Consider, the brain may not always be required to coordinate stimuli received from sensory pathways located in muscle tissue—In fact, much of this processing may occur in the spinal cord. Using an exemplary garment of the embodiments for the retraining and preservation of good posture, this happens unconsciously and requires minimal brain processing or cognitive participation from the user—a user simply has to wear it at times of their own choosing.

In some embodiments, the garments can thus be worn to enhance the data input to the user's nervous system. The amended information is sent via neural sensory pathways to the spinal cord. At the spinal cord, interneurons (relay neurons) encode the information and send edited data back to muscle fibers via neural motor pathways where an action potential is transmitted across a synapse. Finally, an amended reflex action occurs by way of a muscle contraction. Thus, the exemplary garment can employ this method of influencing the innate process of muscle intelligence.

Over time, the posture garments could assist the sensory processing of balance and movement of the wearer by unconsciously participating with innate physiology to induce a learned balance of neuromuscular function. Moreover, the exemplary garments as a posture intervention could facilitate the compromised movement rhythms in sleeping, eating, normal bowel movements, and a body that is free of pain. The posture control system can thus be used a therapy of external leverage.

Although other modifications and changes may be suggested by those skilled in the art, it is the intention of the inventors to embody within the patent warranted hereon all changes and modifications as reasonably and properly come within the scope of their contribution to the art.

I claim:

1. A garment for wear on a lower portion of a body, comprising:
    a lower center back panel having an upper edge, and opposite lower edge, and first and second opposing sides, the upper edge of the lower back panel being configured to be worn with the lower center back panel extending below the waist of the wearer and disposed on a lower back of the wearer;
    first and second waist straps extending from respective ones of the first and second opposing sides of the lower center back panel, the first and second waist straps each having a first end connected to the respective first and second opposing sides of the lower center back panel adjacent the upper edge of the lower center back panel, the first and second waist straps each having a second free end opposite the first end of the first and second waist straps;
    first and second hip straps extending from respective ones of the first and second opposing sides of the lower center back panel, the first and second hip straps each having a first end connected to the respective first and second opposing sides at locations spaced a distance from the upper edge of the lower center back panel, the first and second hip straps each having a second free end opposite the first end of the first and second hip straps;
    a front center panel having an upper edge, an opposite lower edge and first and second opposing sides, the upper edge of the front center panel being configured to be worn along the waist of the wearer at a front of a torso of the wearer;
    fasteners operable for removably fastening the second free ends of the first and second waist straps and the second free ends of the first and second hip straps to the front center panel, the second free ends of the first and second waist straps being removable from and reattachable to the front center panel to enable the wearer to adjust tension on the waist straps and hip straps;
    a crotch panel extending from the lower edge of the lower center back panel to the lower edge of the front center panel;
    first and second leg portions attached to the lower center back panel and to the front center panel and to the crotch panel, each of the first and second leg portions including tubular portions configured for wear on legs of the wearer;
    first and second spiral straps each having first and second opposite ends, the first end of each of the first and second spiral straps being connected to the front center panel, the second opposite end of the first and second spiral straps being connected to respective ones of the first and second leg portions, the first and second spiral straps each configured to spiral around each leg of the wearer, the first and second spiral straps being configured to exert a tension along their length; and
    a cover extending over the front center panel, the cover being attached to the front center panel at the upper edge and at the lower opposite edge, first and second sides of the cover being free of the front center panel and defining first and second openings between the cover and the front center panel, the first and second waist straps and the first and second hip straps extending through the respective openings when the free ends of the waist straps and hip straps are fastened to the front center panel.

2. A garment as claimed in claim 1, wherein the first and second spiral straps each attach to the lower center back panel at a location along the first and second spiral straps between the first and second opposite ends of the spiral straps.

3. A garment as claimed in claim 1, wherein the fasteners include hook and loop fasteners mounted to removably connect the second free ends of the waist straps and the hip straps to the front center panel.

4. A garment as claimed in claim 1, wherein the first and second spiral straps are configured to wrap one and a half times around the respective leg of the wearer.

5. A garment as claimed in claim 1, wherein the garment further comprises first and second fastening sites attached to the respective first and second leg portions and attached to respective first and second spiral straps, and wherein the garment is shorts and wherein the first and second fastening sites are adjacent to hems of the leg portions of the shorts.

6. A garment as claimed in claim 1, further comprising:
first and second hip fastener sites between the central lower back panel and the front center panel.

7. A garment as claimed in claim 6, wherein the first and second hip fastener sites are beneath the first and second hip straps when the first and second hip straps are fastened at their second opposite ends to the front center panel.

8. A garment as claimed in claim 1, wherein the first and second spiral straps each extend away from the front center panel toward respective outward lateral sides of the first and second leg portions and are configured to spiral around each leg of the wearer.

9. A garment for wear on a lower portion of a body, comprising:
a lower center back panel having an upper edge, and opposite lower edge, and first and second opposing sides, the upper edge of the lower back panel being configured to be worn with the lower center back panel extending below the waist of the wearer and disposed on a lower back of the wearer;
first and second waist straps extending from respective ones of the first and second opposing sides of the lower center back panel, the first and second waist straps each having a first end connected to the respective first and second opposing sides of the lower center back panel adjacent the upper edge of the lower center back panel, the first and second waist straps each having a second free end opposite the first end of the first and second waist straps;
first and second hip straps extending from respective ones of the first and second opposing sides of the lower center back panel, the first and second hip straps each having a first end connected to the respective first and second opposing sides at locations spaced a distance from the upper edge of the lower center back panel, the first and second hip straps each having a second free end opposite the first end of the first and second hip straps;
a front center panel having an upper edge, an opposite lower edge and first and second opposing sides, the upper edge of the front center panel being configured to be worn along the waist of the wearer at a front of a torso of the wearer;
fasteners operable for removably fastening the second free ends of the first and second waist straps and the second free ends of the first and second hip straps to the front center panel, the second free ends of the first and second waist straps being removable from and reattachable to the front center panel to enable the wearer to adjust tension on the waist straps and hip straps;
a crotch panel extending from the lower edge of the lower center back panel to the lower edge of the front center panel;
first and second leg portions attached to the lower center back panel and to the front center panel and to the crotch panel, each of the first and second leg portions including tubular portions configured for wear on legs of the wearer;
first and second spiral straps each having first and second opposite ends, the first end of each of the first and second spiral straps being connected to the front center panel, the second opposite end of the first and second spiral straps being connected to respective ones of the first and second leg portions, the first and second spiral straps each configured to spiral around each leg of the wearer, the first and second spiral straps being configured to exert a tension along their length; and
first and second hip fastener sites between the central lower back panel and the front center panel.

10. A garment as claimed in claim 9, wherein the first and second spiral straps each attach to the lower center back panel at a location along the first and second spiral straps between the first and second opposite ends of the spiral straps.

11. A garment as claimed in claim 9, wherein the fasteners include hook and loop fasteners mounted to removably connect the second free ends of the waist straps and the hip straps to the front center panel.

12. A garment as claimed in claim 9, wherein the first and second spiral straps are configured to wrap one and a half times around the respective leg of the wearer.

13. A garment as claimed in claim 9, further comprising:
first and second fastening sites attached to the respective first and second leg portions and attached to respective first and second spiral straps.

14. A garment as claimed in claim 13, wherein the garment is shorts and wherein the first and second fastening sites are adjacent to hems of the leg portions of the shorts.

15. A garment as claimed in claim 13, wherein the first and second fastener sites are first and second leg fastener sites, and further comprising:
at least one further garment is attached to at least one fastener site of the first and second leg fastener sites or both the first and second hip fastener sites, the garment and the at least one further garment are configured to form a garment system.

16. A garment as claimed in claim 9, wherein the first and second spiral straps each extend away from the front center panel toward respective outward lateral sides of the first and second leg portions and are configured to spiral around each leg of the wearer.

17. A system comprising a garment for wear on a lower portion of a body, comprising:
a lower center back panel having an upper edge, and opposite lower edge, and first and second opposing sides, the upper edge of the lower back panel being configured to be worn with the lower center back panel extending below the waist of the wearer and disposed on a lower back of the wearer;
first and second waist straps extending from respective ones of the first and second opposing sides of the lower center back panel, the first and second waist straps each having a first end connected to the respective first and second opposing sides of the lower center back panel adjacent the upper edge of the lower center back panel, the first and second waist straps each having a second free end opposite the first end of the first and second waist straps;

first and second hip straps extending from respective ones of the first and second opposing sides of the lower center back panel, the first and second hip straps each having a first end connected to the respective first and second opposing sides at locations spaced a distance from the upper edge of the lower center back panel, the first and second hip straps each having a second free end opposite the first end of the first and second hip straps;

a front center panel having an upper edge, an opposite lower edge and first and second opposing sides, the upper edge of the front center panel being configured to be worn along the waist of the wearer at a front of a torso of the wearer;

fasteners operable for removably fastening the second free ends of the first and second waist straps and the second free ends of the first and second hip straps to the front center panel, the second free ends of the first and second waist straps being removable from and reattachable to the front center panel to enable the wearer to adjust tension on the waist straps and hip straps;

a crotch panel extending from the lower edge of the lower center back panel to the lower edge of the front center panel;

first and second leg portions attached to the lower center back panel and to the front center panel and to the crotch panel, each of the first and second leg portions including tubular portions configured for wear on legs of the wearer;

first and second spiral straps each having first and second opposite ends, the first end of each of the first and second spiral straps being connected to the front center panel, the second opposite end of the first and second spiral straps being connected to respective ones of the first and second leg portions, the first and second spiral straps each configured to spiral around each leg of the wearer, the first and second spiral straps being configured to exert a tension along their length;

first and second fastening sites attached to the respective first and second leg portions and attached to respective first and second spiral straps, wherein the first and second fastener sites are first and second leg fastener sites;

first and second hip fastener sites between the central lower back panel and the front center panel; and at least one further garment is attached to at least one fastener site of the first and second leg fastener sites or both the first and second hip fastener sites, wherein the garment and the at least one further garment are configured to form a garment system.

18. A garment as claimed in claim 17, wherein the first and second spiral straps each attach to the lower center back panel at a location along the first and second spiral straps between the first and second opposite ends of the spiral straps.

19. A garment as claimed in claim 17, wherein the first and second spiral straps each extend away from the front center panel toward respective outward lateral sides of the first and second leg portions and are configured to spiral around each leg of the wearer.

* * * * *